US008663912B2

(12) United States Patent
Sadler et al.

(10) Patent No.: US 8,663,912 B2
(45) Date of Patent: Mar. 4, 2014

(54) FLUOROGENIC SUBSTRATE FOR ADAMTS13

(75) Inventors: J. Evan Sadler, St. Louis, MO (US); Joshua Muia, St. Louis, MO (US); Weiqiang Gao, St. Louis, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 13/552,272

(22) Filed: Jul. 18, 2012

(65) Prior Publication Data

US 2013/0023004 A1 Jan. 24, 2013

Related U.S. Application Data

(60) Provisional application No. 61/508,782, filed on Jul. 18, 2011.

(51) Int. Cl.
*C12Q 1/00* (2006.01)
*A61K 38/00* (2006.01)

(52) U.S. Cl.
USPC ............................ 435/4; 530/324; 530/300

(58) Field of Classification Search
None
See application file for complete search history.

(56) References Cited

U.S. PATENT DOCUMENTS

| 7,468,258 B2 | 12/2008 | Owen |
| 7,927,864 B2 | 4/2011 | Owen |
| 2010/0240050 A1 | 9/2010 | Bhatia et al. |

OTHER PUBLICATIONS

Alexa Fluor 594 Fluronagold Product Information Sheet, 2009.*
Adachi, T., et al., "High titer of ADAMTS13 inhibitor associated with thrombotic microangiopathy of the gut and skeletal muscle after allogeneic hematopoietic stem cell transplantation." Int. J. Hematol. 83:415-9,2006.
Anderson, PJ., et al., "Zinc and calcium ions cooperatively modulate ADAMTSI3 activity." J. Bioi. Chem. 281 :850-7, 2006.
Coppo, P., et al., "Severe ADAMTS13 deficiency in adult idiopathic thrombotic microangiopathies defines a subset of patients characterized by various autoimmune manifestations, lower platelet count, and mild renal involvement." Medicine. 83:233-244, 2004.
Dayananda, K.M., et al., "*Escherichia coli*-derived von Willebrand factor-A2 domain fluorescence/Förster resonance energy transfer proteins that quantify ADAMTS13 activity." Anal Biochem. 410:206-13, 2011.
Downes, K.A., et al., "Relapsed thrombotic thrombocytopenic purpura presenting as an acute cerebrovascular accident." J. Clin. Apher. 19:86-89, 2004.
Fujisaki, K, et al., "Thrombotic thrombocytopenic purpura associated with polyarteritis nodosa." Clin Nephrol. 64:305-310, 2005.
George, J.N., "The association of pregnancy with thrombotic thrombocytopenic purpura hemolytic uremic syndrome." Curr Opin. Hematol. 10:339-344, 2003.
Gerritsen, H.E., et al., "Partial amino acid sequence of purified von Willebrand factor-cleaving protease." Blood. 98:1654-1661, 2001.
Groot, E., et al., "FRETS-VWF73: a rapid and predictive tool for thrombotic thrombocytopenic purpura." J. Thromb. Haemost. 4:698-699,2006.
Hovinga, J.A.K., et al., "Survival and relapse in patients with thrombotic thrombocytopenic purpura." Blood. 115:1500-11, 2010.
Jin, M., et al., "A rapid test for the diagnosis of thrombotic thrombocytopenic purpura using surface enhanced laser desorption/ionization time-of-flight (SELDI-TOF)-mass spectrometry." J Thromb Haemost. 4:333-338, 2006.
Jin, M., et al., "Relationship between ADAMTS13 activity in clinical remission and the risk of TTP relapse." Br J Haematol. 141:651-658, 2008.
Kokame, K., et al., "FRETS-VWF73, a first fluorogenic substrate for ADAMTS13 assay." Br. J. Haematol. 129:93-100, 2005.
Kremer Hovinga, J .A., et al., "Measurement of Adamts-13 activity in plasma by the FRETSVWF73 assay: comparison with other assay methods." J. Thromb. Haemost. 4:1146-1148, 2006.
Lattuada, A., et al., "Mild to moderate reduction of a von Willebrand factor cleaving protease (ADAMTS-13) in pregnant women with HELLP microangiopathic syndrome." Haematologica. 88:1029-1034, 2003.
Mal, H., et al., "Thrombotic microangiopathy with acquired deficiency in ADAMTS 13 activity in lung transplant recipients." Transplantation. 81: 1628-1632, 2006.
Meyer, S.C., et al., "Hyperbilirubinemia interferes with ADAMTS-13 activity measurement by FRETS-VWF73 assay: diagnostic relevance in patients suffering from acute thrombotic microangiopathies." J. Thromb. Haemost. 5:866-7, 2007.
Palla, R., et al., "Evaluation of assay methods to measure plasma ADAMTS13 activity in thrombotic microangiopathies." Thromb Haemost. 105:381-5, 2011.
Peyvandi, F., et al., "ADAMTS-13 assays in thrombotic thrombocytopenic purpura." J. Thromb. Haemost. 8:631-640, 2010.
Pham, P.T., et al., "Inhibitors of ADAMTSI3: a potential factor in the cause of thrombotic microangiopathy in a renal allograft recipient." Transplantation. 74:1077-1080, 2002.
Rick, M.E., et al., "Clinical usefulness of a functional assay for the von Willebrand factor cleaving protease (ADAMTS 13) and its inhibitor in a patient with thrombotic thrombocytopenic purpura." Am. J. Hematol. 75:96-100, 2004.

(Continued)

*Primary Examiner* — Shulamith H Shafer
(74) *Attorney, Agent, or Firm* — Saul L. Zackson; Zackson Law LLC

(57) ABSTRACT

Disclosed are fluorogenic substrates for measuring ADAMTS13 activity or ADAMTS13 inhibitor activity. Substrates can comprise an oligopeptide which can consist of up to 80 amino acids of sequence of von Willebrand Factor (VWF). The oligopeptide can include modifications of sequence of VWF, including an amino-terminal glycine, a scissile Y-M peptide, and a cysteine substitution located from 1 to 12 amino acids from the scissile Y-M in the carboxy terminal direction. A substrate can further comprise a fluorophore and a fluorescence quencher bound to the oligopeptide on opposite sides of the scissile Y-M peptide, wherein the fluorescence quencher is not identical to the fluorophore. An oligopeptide can be encoded by a nucleic acid sequence which can also encode a His tag. An oligopeptide can be expressed in a cell or microorganism. Also disclosed are methods of using a fluorogenic substrate to measure ADAMTS13 activity or ADAMTS13 inhibitor activity.

19 Claims, 8 Drawing Sheets

(56) References Cited

OTHER PUBLICATIONS

Studt, J.D., et al., "Fatal congenital thrombotic thrombocytopenic purpura with apparent ADAMTS13 inhibitor: in vitro inhibition of ADAMTS13 activity by hemoglobin." Blood. 105:542-4, 2005.

Tripodi, A., et al., "Second international collaborative study evaluating performance characteristics of methods measuring the von Willebrand factor cleaving protease(ADAMTS-13)." J. Thromb. Haemost. 6:1534-1541, 2008.

Tsai, H.M., "Physiologic cleavage of von Willebrand factor by a plasma protease is dependent on its conformation and requires calcium ion." Blood. 87:4235-44, 1996.

Zhang, L., et al., "Creation of a recombinant peptide substrate for fluorescence resonance energy transfer-based protease assays." Anal Biochem. 358:298-300, 2006.

Zheng, X.L., et al., "Effect of plasma exchange on plasma ADAMTS 13 metalloprotease activity, inhibitor level, and clinical outcome in patients with idiopathic and nonidiopathic thrombotic thrombocytopenic purpura." Blood. 103:4043-4049, 2004.

* cited by examiner

FLUOROGENIC SUBSTRATE FOR ADAMTS13

CROSS-REFERENCE TO RELATED APPLICATIONS

This application claims priority to U.S. Provisional Application Ser. No. 61/508,782 filed on Jul. 18, 2011, which is incorporated herein by reference in its entirety.

STATEMENT REGARDING FEDERALLY SPONSORED RESEARCH OR DEVELOPMENT

This invention was made with government support under Grants R01 HL072917-08 and R01 HL089746-04 awarded by the National Institutes of Health. The Government has certain rights in the invention.

INCORPORATION-BY-REFERENCE OF MATERIAL SUBMITTED IN COMPUTER READABLE FORM

The Sequence Listing, which is a part of the present disclosure, includes a computer readable form. The subject matter of the Sequence Listing is incorporated herein by reference in its entirety. The information recorded in computer readable form is identical to the written sequence listing.

INTRODUCTION

ADAMTS13 is a metalloprotease that cleaves von Willebrand Factor (VWF) and inhibits the growth of platelet thrombi. ADAMTS13 is a normal component of blood. In some disease states, such as, for example idiopathic thrombotic thrombocytopenic purpura (idiopathic TTP), levels of ADAMTS13 levels can be below normal.

Several studies suggest that ADAMTS13 activity and inhibitor assays can provide useful prognostic information. Measurement of ADAMTS13 activity in blood, plasma or serum can be useful, for example to identify patients with severe ADAMTS13 deficiency (Tsai, H-M.; Blood. 87:4235-4244, 1996; Downes, K. A., et al., J. Clin. Apheresis. 19:86-89, 2004), or with confounding potential causes of thrombotic microangiopathy such as stem cell (Adachi, T., et al., Int. J. Hematol. 83:415-419, 2006) or solid organ transplants (Pham, P. T., et al., Transplantation. 74:1077-1080, 2002; Mal, H., et al., Transplantation. 81:1628-1632, 2006), systemic lupus erythematosis (Ahmed, S., et al., Am J. Med. 116:786-787, 2004; Rick, M. E., et al., Am. J. Hematol. 75:96-100, 2004; Fujisaki, K., et al., Clin Nephrol. 64:305-310, 2005; Coppo, P., et al., Medicine. 83:233-244, 2004), preeclampsia or HELLP syndrome (Lattuada, A et al., Haematologica. 88:1029-1034, 2003; George, J. N., Curr. Opin. Hematol. 10:339-344, 2003). In such situations, ADAMTS13 testing can facilitate diagnosis and expedite treatment.

However, the clinical use of ADAMTS13 data requires assays that are rapid, robust, and feasible for most hospital laboratories. Available assays for ADAMTS13 activity can be technically challenging, slow to perform, insensitive to inhibitors, and difficult to automate (Furlan, M., et al., Blood. 87:4223-4234, 1996; Gerritsen, H. E., et al., Thromb Haemost. 82:1386-1369, 1999).

FRETS-VWF73 is a fluorogenic ADAMTS13 substrate that corresponds to VWF $Asp^{1596}$-$Arg^{1668}$ (73 residues), replacing $Gln^{1599}$ with 2,3-diaminopropionic acid (A2pr) linked to N-methyl anthranilate (Nma), and $Asn^{1610}$ with A2pr-2,4-dinitrophenyl (Dnp) (Kokame, K., et al., Br. J. Haematol. 129:93-100, 2005). In FRETS-VWF73, $Gln^{1599}$ is replaced with A2pr (Nma), and $Asn^{1610}$ is replaced with A2pr (Dnp). Nma absorbs at 340 nm and emits at 440 nm; nearby Dnp quenches this fluorescence. When the $Tyr^{1605}$-$Met^{1606}$ bond is cleaved, quenching is relieved, producing a fluorescence signal proportional to product concentration. FRETS-VWF73 assays require <1 hour and have been adapted to measure inhibitors. Results with FRETS-VWF73 and multimeric VWF substrates are generally congruent (Kokame, K., et al., Br. J. Haematol. 129:93-100, 2005; Kremer Hoving a, J. A., et al., J. Thromb. Haemost. 4:1146-1148, 2006; Groot, E., et al., J. Thromb. Haemost. 4:698-699, 2006; Tripodi, A., et al., J. Thromb. Haemost. 6:1534-1541, 2008; Peyvandi, F., et al., J. Thromb. Haemost. 8:631-640, 2010).

Despite these attributes, FRETS-VWF73 has several limitations. For example, it is chemically synthesized, and expensive (~$10/data point). Furthermore, assay conditions are not physiological (pH 6.0, low ionic strength) (Kokame, K., et al., Br. J. Haematol. 129:93-100, 2005). Nma absorption at 340 nm and emission at 450 nm make assays susceptible to interference from autofluorescence, absorbance and quenching by plasma proteins such as hemoglobin and bilirubin (Meyer, S. C., et al., J. Thromb. Haemost. 5:866-867, 2007). To avoid such problems, in these methods plasma is diluted ≥1:20 in ADAMTS13 assays using FRETS-VWF73 substrate. This dilution limits assay sensitivity to ~3% of normal ADAMTS13 levels, prevents the detection of some inhibitors, and can overestimate ADAMTS13 activity for patients with low titer inhibitors (Kremer Hovinga, J. A., et al., Blood. 115:1500-1511, 2010).

Current assays of ADAMTS13 involve dilutions of ≥1:20 and cannot detect inhibitors with low affinity and rapid dissociation kinetics. Alternatively, ELISA methods are used that measure antibody bound to immobilized ADAMTS13 and results are reported as "μg antibody/mL," analogous to assays for anti-PF4 antibodies. However, this approach cannot distinguish inhibitory from noninhibitory antibodies that may have no biological significance.

United States Patent Application 20100240050 of Bhatia, S. N., et al., entitled "Methods and Products For In Vivo Enzyme Profiling." discloses a "pro-diagnostic reagent" comprising "a carrier domain linked to an enzyme susceptible domain which is linked to a signature molecule." A "signature molecule" can be a peptide, nucleic acid, small molecule, fluorophore/quencher, carbohydrate, or particle, such as a peptide comprising a fluorophore and a quencher. However, the carrier domain comprises a particle, for example, a microparticle or a nanoparticle. Although this publication lists ADAMTS13 and VWF as an enzyme and substrate, none of the peptide sequences disclosed in this application appear to derive from VWF or could be used as a target substrate for ADAMTS13.

U.S. Pat. Nos. 7,468,258 and 7,927,864 to Owen disclose a peptide consisting of a sequence from VWF which further comprises self-quenching fluorophores. This fluorogenic ADAMTS13 substrate relies on the autoquenching properties of the disclosed paired fluorophores as an alternative to fluorophore-quencher combinations.

However, there is an unmet need for an ADAMST13 substrate that can be used with minimal sample dilution.

SUMMARY

The present inventors have developed fluorogenic substrates which can be used to measure ADAMTS13 activity as well as ADAMTS13 inhibitor activity. An ADAMTS13 substrate of the present teachings comprises an oligopeptide. In some embodiments, an oligopeptide of the present teachings can be encoded in a vector and expressed in a cell or a microorganism such as E. coli. An ADAMTS13 substrate of the present teachings can further comprise a fluorophore and a fluorescence quencher.

In some embodiments, a fluorogenic ADAMTS13 substrate of the present teachings comprises an oligopeptide consisting of no more than 80 amino acids of sequence of von Willebrand Factor (VWF). In various embodiments, the oligopeptide can comprise a scissile tyrosine-methionine (Y-M) peptide, a cysteine substitution located from 1 to 12 amino acids from the scissile Y-M in the carboxy terminal direction; a C-terminal segment; a fluorophore; and a fluorescence quencher.

In some configurations, an oligopeptide of an ADAMTS13 substrate can consist of no more than 73 amino acids. In some configurations, an oligopeptide of an ADAMTS13 substrate can consist of no more than 72 amino acids. In some configurations, an oligopeptide of an ADAMTS13 substrate can consist of no more than 71 amino acids.

In some configurations, the cysteine substitution can be situated 3 amino acids from the scissile Y-M peptide. In some configurations, the cysteine substitution can be a N1610C substitution of a VWF sequence.

In some configurations, an oligopeptide can comprise a substitution of lysine K 1617 for an amino acid that does not comprise a primary amine on its side chain that can react with amine-reactive reagents (such as a succinimidyl ester or an isothiocyanate). In some configurations, an oligopeptide can comprise a K1617R substitution.

In some configurations, an oligopeptide can comprise a substitution of glutamic acid E1798 of VWF with glycine, so that the oligopeptide comprises a glycine at its amino terminal.

In some configurations, a probe can comprise an oligopeptide consisting of a sequence set forth as SEQ ID NO: 1:

DREQAPNLVYMVTGCPASDEIKRLPGDIQVVPIGVGPNANVQELERIGW

PNAPILIQDFETLPREAPDLVLQR.

In some configurations, a probe can comprise an oligopeptide consisting of a sequence set forth as SEQ ID NO: 2:

GQAPNLVYMVTGCPASDEIRRLPGDIQVVPIGVGPNANVQELERIGWPN

APILIQDFETLPREAPDLVLQR.

In various aspects, an ADAMTS13 substrate of the present teachings can comprise a fluorophore and a fluorescence quencher situated on opposite sides of a scissile Y-M peptide. In various configurations, a fluorophore can have an absorption maximum of >550 nm or >630 nm.

In various aspects, a fluorophore can have an emission maximum of >600 nm or >650 nm.

In some aspects, a fluorophore can comprise at least one sulfate.

In some aspects, a fluorophore can be an Alexa Fluor® 594 maleimide (Life Technologies Corporation, Carlsbad, Calif.) or a DyLight® 633 maleimide (Thermo Fisher Scientific, Rockford, Ill.).

In various aspects, a quencher can have an absorption maximum of >550 nm or >630 nm.

In some aspects, a quencher can comprise at least one sulfate.

In some aspects, a quencher can be a QSY21-succinimidyl ester or an IRDye QC-1 N-hydroxy succinimidyl ester.

In some aspects, a probe can be soluble in water at >50 µM.
In some aspects, a probe can be soluble in water at >200 µM.

In some embodiments, the present teachings include a vector comprising a nucleic acid sequence encoding an oligopeptide of an ADAMTS13 substrate described herein.

In some aspects, a nucleic acid sequence can further encode an N-terminal His tag.

In some aspects, a nucleic acid sequence can further comprise a sequence encoding thioredoxin.

In some aspects, a nucleic acid sequence can further comprise a sequence encoding an oligopeptide further comprises a sequence encoding a Tobacco Etch Virus (TEV) protease cleavage site.

In some aspects, a vector can be a plasmid or a virus, such as a bacteriophage.

In some embodiments, the present teachings include methods of determining presence, absence or quantity of ADAMTS13 activity in a sample.

In some embodiments, the inventors disclose assays for detecting and quantifying activity of inhibitors of ADAMTS13. In some configurations, an assay of the present teachings can be substantially more sensitive than alternative existing assays for detecting inhibitors of ADAMTS13.

In various configurations, methods of the present teachings can comprise: forming a mixture comprising a sample and a probe as described herein; and measuring fluorescence at one or more time points after forming the mixture.

In some configurations, the sample can be a blood sample, a serum sample, or a plasma sample.

In some configurations, the sample can be undiluted or diluted less than 20-fold in an assay of ADAMTS13 activity or ADAMTS13 inhibitor activity. In some configurations, the sample can be diluted less than 2-fold. In some configurations, the sample can be heparinized plasma. In some configurations, the sample can be citrated plasma. In some configurations, the sample can be serum. In some configurations, the sample can be plasma anticoagulated with any protease inhibitor that does not interfere with ADAMTS13 activity.

In some aspects, an ADAMTS13 assay or ADAMTS13 inhibitor assay using a probe of the present teachings can be insensitive to >20 mg/dL (250 µM) conjugated bilirubin.

In some configurations, sensitivity of assays for inhibitors of ADAMTS13 activity can be increased by using recombinant ADAMTS13 (including concentrated recombinant ADAMTS13) as the enzyme source instead of pooled normal plasma.

In some embodiments, the present teachings include methods of producing a probe described herein.

In some configurations, these methods can comprise expressing, in a cell, an oligopeptide encoded by a vector described herein. Alternatively, an oligopeptide can be generated by chemical means such as, for example but not limited to, the solid-phase method of Merrifield, R., J. Am. Chem. Soc. 85: 2149-2154, 1963. In various configurations, an oligopeptide can be digested with His-tagged TEV protease to yield an oligopeptide comprising VWF sequence comprising a cysteine as described herein. In various configurations, an oligopeptide comprising a cysteine can be reacted with a fluorophore comprising a maleimide. In various configurations, an oligopeptide can comprise a primary amine such as the N-terminal primary amine which can be reacted with a fluorescence quencher comprising a succinimidyl ester or other amine-reactive moiety such as, without limitation, an isothiocyanate.

Alternatively, an oligopeptide can be generated by chemical means such as, for example but not limited to, the solid-phase method of Merrifield, R., J. Am. Chem. Soc. 85: 2149-2154, 1963. In various configurations, an oligopeptide can be digested with His-tagged TEV protease to yield an oligopeptide comprising VWF sequence comprising a cysteine as described herein. In various configurations, an oligopeptide comprising a cysteine can be reacted with a fluorescence quencher comprising a maleimide. In various configurations, an oligopeptide can comprise a primary amine such as the N-terminal primary amine which can be reacted with a fluorophore comprising a succinimidyl ester or other amine-reactive moiety such as, without limitation, an isothiocyanate. The present disclosure includes the following aspects, without limitation:

1. A probe comprising:
    an oligopeptide consisting of no more than 80 amino acids of sequence of von Willebrand Factor (VWF), said oligopeptide comprising a scissile Y-M peptide, a cysteine substitution located from 1 to 12 amino acids from the scissile Y-M in the carboxy terminal direction, and a C-terminal segment;
    a fluorophore; and
    a fluorescence quencher,
wherein the fluorophore and the fluorescence quencher are bound to the oligopeptide on opposite sides of the scissile Y-M peptide.
2. A probe in accordance with aspect 1, wherein the oligopeptide consists of no more than 73 amino acids.
3. A probe in accordance with aspect 1, wherein the oligopeptide consists of no more than 71 amino acids.
4. A probe in accordance with aspect 1, wherein the cysteine substitution is situated 3 amino acids from the scissile Y-M peptide.
5. A probe in accordance with aspect 1, wherein the cysteine substitution is a N1610C substitution of a VWF sequence.
6. A probe in accordance with aspect 1, wherein the oligopeptide comprises a substitution of lysine K1617 for an amino acid that does not comprise a primary amine on its side chain.
7. A probe in accordance with aspect 1, comprising a K1617R substitution.
8. A probe in accordance with aspect 1, wherein the oligopeptide consists of the sequence set forth as SEQ ID NO: 2,

GQAPNLVYMVTGCPASDEIRRLPGDIQVVPIGVGPNANVQELERIGWPN

APILIQDFETLPREAPDLVLQR.

9. A probe in accordance with aspect 1, wherein the fluorophore has an absorption maximum >550 nm.
10. A probe in accordance with aspect 1, wherein the fluorophore has an emission maximum >600 nm.
11. A probe in accordance with aspect 1, wherein the fluorophore has an absorption maximum >630 nm.
12. A probe in accordance with aspect 1, wherein the fluorophore has an emission maximum >650 nm.
13. A probe in accordance with aspect 1, wherein the fluorophore comprises at least one sulfate.
14. A probe in accordance with aspect 1, wherein the fluorophore is Alexa Fluor 594 maleimide.
15. A probe in accordance with aspect 1, wherein the fluorophore is DyLight 633 maleimide.
16. A probe in accordance with aspect 1, wherein the quencher has an absorption maximum >550 nm.
17. A probe in accordance with aspect 1, wherein the quencher has an absorption maximum >630 nm.
18. A probe in accordance with aspect 1, wherein the quencher comprises at least one sulfate.
19. A probe in accordance with aspect 1, wherein the quencher is QSY21-succinimidyl ester.
20. A probe in accordance with aspect 1, wherein the quencher is IRDye QC-1 N-hydroxy succinimidyl ester.
21. A probe in accordance with aspect 1, wherein the quencher is attached to the oligopeptide at the amino terminal of the oligopeptide.
22. A probe in accordance with aspect 1, wherein the fluorophore is attached to the oligopeptide at the cysteine.
23. A probe in accordance with aspect 1, wherein the probe is soluble in water at >50 μM.
24. A vector comprising a nucleic acid sequence encoding an oligopeptide of aspect 1.
25. A vector in accordance with aspect 24, further comprising a nucleic acid sequence encoding an N-terminal His tag.
26. A vector in accordance with aspect 24, wherein the nucleic acid sequence encoding an oligopeptide further comprises a sequence encoding thioredoxin.
27. A vector in accordance with aspect 24, wherein the nucleic acid sequence encoding an oligopeptide further comprises a sequence encoding a Tobacco Etch Virus (TEV) protease cleavage site.
28. A vector in accordance with aspect 24, wherein the vector is a plasmid.
29. A method of determining presence, absence or quantity of ADAMTS13 activity in a sample, comprising:
    forming a mixture comprising a sample and a probe of aspect 1; and
    measuring fluorescence at one or more time points after forming the mixture, wherein the sample is diluted less than 20-fold.
30. A method in accordance with aspect 29, wherein the sample is a serum sample.
31. A method in accordance with aspect 30, wherein the serum sample is an undiluted serum sample.
32. A method in accordance with aspect 30, wherein the serum sample is a concentrated serum sample.
33. A method in accordance with aspect 29, wherein the sample is a plasma sample.
34. A method in accordance with aspect 33, wherein the plasma sample is an undiluted plasma sample.
35. A method in accordance with aspect 33, wherein the plasma sample is a concentrated plasma sample.
36. A method of determining presence, absence or quantity of ADAMTS13 inhibitor activity in a sample, comprising:
    forming a mixture comprising a sample, a source of ADAMTS13, and a probe of aspect 1; and
    measuring fluorescence at one or more time points after forming the mixture.
37. A method in accordance with aspect 36, further comprising inactivating ADAMTS13 activity endogenous to the sample prior to forming the mixture.
38. A method in accordance with aspect 37, wherein the inactivating ADAMTS13 activity comprises heating the sample.
39. A method in accordance with aspect 38, wherein the heating the sample comprises heating the sample to about 56° C. for about 30 min.
40. A method in accordance with aspect 36, wherein the source of ADAMTS13 is selected from the group consisting of normal plasma, recombinant ADAMTS13, and a combination thereof.
41. A method in accordance with aspect 36, wherein the sample is a serum sample.
42. A method in accordance with aspect 41, wherein the serum sample is an undiluted serum sample.

43. A method in accordance with aspect 41, wherein the serum sample is a concentrated serum sample.
44. A method in accordance with aspect 36, wherein the sample is a plasma sample.
45. A method in accordance with aspect 44, wherein the plasma sample is an undiluted plasma sample.
46. A method in accordance with aspect 44, wherein the plasma sample is a concentrated plasma sample.
47. A method of producing a probe of aspect 1, comprising:
expressing in a cell, an oligopeptide encoded by the vector of aspect 24;
digesting the oligopeptide with His-tagged TEV protease to yield an oligopeptide comprising VWF sequence comprising a cysteine of aspect 5; and
reacting the cysteine with a fluorophore comprising a maleimide, and reacting a primary amine of the oligopeptide such as the N-terminal primary amine with a fluorescence quencher comprising a succinimidyl ester.

DETAILED DESCRIPTION

Figure 1:
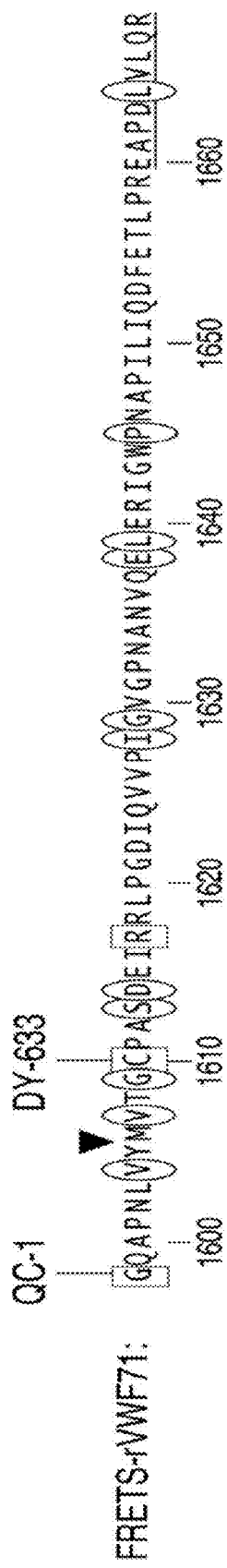
FIG. 1 illustrates an optimized fluorogenic ADAMTS13 substrate set forth as SEQ ID No: 2.

The present inventors have developed fluorogenic substrates which can be used to measure ADAMTS13 activity. An ADAMTS13 substrate of the present teachings comprises an oligopeptide which can be encoded in a vector and expressed in a cell or a microorganism such as E. coli. ADAMTS13 substrate of the present teachings can further comprise a fluorophore and fluorescence quencher.

The present inventors have shown that the substrate, FRETS-rVWF71, can be cleaved by ADAMTS13 and that it can be used as an ADAMTS13 substrate without significant interference in undiluted serum or plasma. Contact between a probe of the present teachings and ADAMTS13 can lead to cleavage of the probe which can result in a positive signal, i.e., an increase in fluorescence. In various configurations, the increase in fluorescence can be quantified and can serve as a measure of ADAMTS13 activity comprised by a sample. Furthermore, the quantifiable fluorescence signal can be used to measure ADAMTS13 inhibitor activity in a sample.

In various configurations, FRETS-rVWF71 allows ADAMTS13 activity and ADAMTS13 inhibitor activity assays to be performed in undiluted plasma or serum. In various configurations of the present teachings, an assay using FRETS-rVWF71 can be approximately 8-fold more sensitive than an assay using FRETS-VWF73, when using equal concentrations of plasma as the enzyme source. In various configurations, FRETS-rVWF71 can be used in undiluted plasma, which can increase sensitivity another 30-fold relative to FRETS-VWF73, or 240-fold overall. Because the substrate can be used in undiluted plasma, it can be used to detect ADAMTS13 inhibitors that have not been possible to detect with FRETS-VWF73.

In some embodiments, the inventors disclose assays for detecting and quantifying activity of inhibitors of ADAMTS13. In some configurations, an assay of the present teachings can be substantially more sensitive than alternative assays for detecting inhibitors of ADAMTS13. In some configurations, an assay of the present teachings can detect inhibitor activity at <0.5 "Bethesda-like Units" (BU) per mL. For example, a sample from a subject with TTP and undetectable ADAMTS13 activity, and in which a FRETS-VWF73-based assay reported an inhibitor titer ≤1 U/ml. The same sample tested with a FRETS-rVWF71-based assay of the present teachings revealed an inhibitor titer of 6 U/ml.

In some configurations, sensitivity to inhibitors can be increased by using concentrated recombinant ADAMTS13 as the enzyme source instead of pooled normal plasma.

In some embodiments, an ADAMTS13 substrate of the present teachings can be a probe comprising an oligopeptide consisting of no more than 80 amino acids of sequence of von Willebrand Factor (VWF), wherein said oligopeptide comprises a scissile Y-M peptide, a cysteine substitution located from 1 to 12 amino acids from the scissile Y-M in the carboxy terminal direction, and a C-terminal segment; a fluorophore; and a fluorescence quencher. In some configurations, an oligopeptide of an ADAMTS13 substrate can consist of no more than 73 amino acids. In some configurations, an oligopeptide of an ADAMTS13 substrate can consist of no more than 71 amino acids.

In some configurations, the cysteine substitution can be situated 3 amino acids from the scissile Y-M peptide. In some configuration s, the cysteine substitution can be a N1610C substitution of a VWF sequence, wherein the entire sequence of human VWF is:

(Genbank GenBank: AAB59458.1).

(SEQ ID NO: 3)

```
  1 miparfagvl lalalilpgt lcaegtrgrs starcslfgs dfvntfdgsm ysfagycsyl
 61 laggcqkrsf siigdfqngk rvslsvylge ffdihlfvng tvtqgdqrvs mpyaskglyl
121 eteagyykls geaygfvari dgsgnfqvll sdryfnktcg lcgnfnifae ddfmtqegtl
181 tsdpydfans walssgeqwc erasppsssc nissgemqkg lweqcqllks tsvfarchpl
241 vdpepfvalc ektlcecagg lecacpalle yartcaqegm vlygwtdhsa cspvcpagme
```

-continued

```
 301 yrqcvspcar tcqslhinem cqercvdgcs cpegqlldeg lcvestecpc vhsgkryppg
 361 tslsrdcntc icrnsqwics neecpgeclv tgqshfksfd nryftfsgic qyllardcqd
 421 hsfsivietv qcaddrdavc trsvtvrlpg lhnslvklkh gagvamdgqd iqlpllkgdl
 481 riqhtvtasv rlsygedlqm dwdgrgrllv klspvyagkt cglcgnyngn qgddfltpsg
 541 laeprvedfg nawklhgdcq dlqkqhsdpc alnprmtrfs eeacavltsp tfeachravs
 601 plpylrncry dvcscsdgre clcgalasya aacagrgvrv awrepgrcel ncpkgqvylq
 661 cgtpcnltcr slsypdeecn eaclegcfcp pglymdergd cvpkaqcpcy ydgeifqped
 721 ifsdhhtmcy cedgfmhctm sgvpgsllpd avlssplshr skrslscrpp mvklvcpadn
 781 lraeglectk tcqnydlecm smgcvsgclc ppgmvrhenr cvalercpcf hqgkeyapge
 841 tvkigcntcv crdrkwnctd hvcdatcsti gmahyltfdg lkylfpgecq yvlvqdycgs
 901 npgtfrilvg nkgcshpsvk ckkrvtilve ggeielfdge vnvkrpmkde thfevvesgr
 961 yiilllgkal svvwdrhlsi svvlkqtyqe kvcglcgnfd giqnndltss nlqveedpvd
1021 fgnswkvssq cadtrkvpld sspatchnni mkqtmvdssc riltsdvfqd cnklvdpepy
1081 ldvciydtcs cesigdcacf cdtiaayahv caqhgkvvtw rtaticpqsc eernlrengy
1141 ecewrynsca pacqvtcqhp eplacpvqcv egchahcppg kildellqtc vdpedcpvce
1201 vagrrfasgk kvtlnpsdpe hcqichcdvv nltceacqep gglvvpptda pvspttlyve
1261 disepplhdf ycsrlldlvf lldgssrlse aefevlkafv vdmmerlris qkwvrvavve
1321 yhdgshayig lkdrkrpsel rriasqvkya gsqvastsev lkytlfqifs kidrpeasri
1381 alllmasqep qrmsrnfvry vqglkkkkvi vipvgigpha nlkqirliek qapenkafvl
1441 ssvdeleqqr deivsylcdl apeappptlp phmaqvtvgp gllgvstlgp krnsmvldva
1501 fvlegsdkig eadfnrskef meevqrmdv gqdsihvtvl qysymvtvey pfseaqskgd
1561 ilqrvreiry qggnrtntgl alrylsdhsf lvsqgdreqa pnlvymvtgn pasdeikrlp
1621 gdiqvvpigv gpnanvqele rigwpnapil iqdfetlpre apdlvlqrcc sgeglqiptl
1681 spapdcsqpl dvillldgss sfpasyfdem ksfakafisk anigprltqv svlqygsitt
1741 idvpwnvvpe kahllslvdv mqreggpsqi gdalgfavry ltsemhgarp gaskavvilv
1801 tdvsvdsvda aadaarsnrv tvfpigigdr ydaaqlrila gpagdsnvvk lqriedlptm
1861 vtlgnsflhk lcsgfvricm dedgnekrpg dvwtlpdqch tvtcqpdgqt llkshrvncd
1921 rglrpscpns qspvkveetc gcrwtcpcvc tgsstrhivt fdgqnfkltg scsyvlfqnk
1981 eqdlevilhn gacspgarqg cmksievkhs alsvelhsdm evtvngrlvs vpyvggnmev
2041 nvygaimhev rfnhlghift ftpqnnefql qlspktfask tyglcgicde ngandfmlrd
2101 gtvttdwktl vqewtvqrpg qtcqpileeq clvpdsshcq vlllplfaec hkvlapatfy
2161 aicqqdschq eqvceviasy ahlcrtngvc vdwrtpdfca mscppslvyn hcehgcprhc
2221 dgnvsscgdh psegcfcppd kvmlegscvp eeactqcige dgvqhqflea wvpdhqpcqi
2281 ctclsgrkvn cttqpcptak aptcglceva rlrqnadqcc peyecvcdpv scdlppvphc
2341 erglqptltn pgecrpnftc acrkeeckrv sppscpphrl ptlrktqccd eyecacncvn
2401 stvscplgyl astatndcgc ttttclpdkv cvhrstiypv gqfweegcdv ctctdmedav
2461 mglrvaqcsq kpcedscrsg ftyvlhegec cgrclpsace vvtgsprgds qsswksvgsq
2521 waspenpcli necvrvkeev fiqqrnvscp qlevpvcpsg fqlscktsac cpscrcerme
2581 acmlngtvig pgktvmidvc ttcrcmvqvg visgfklecr kttcnpcplg ykeenntgec
2641 cgrclptact iqlrggqimt lkrdetlqdg cdthfckvne rgeyfwekrv tgcppfdehk
```

```
2701 claeggkimk ipgtccdtce epecnditar lqyvkvgsck sevevdihyc qgkcaskamy 2761 sidindvqdq csccsptrte pmqvalhctn gsvvyhevln ameckcsprk csk
```

In some aspects, an oligopeptide of the present teachings can comprise, prior to derivatization, a thiol (—SH) such as a cysteine, for example a N1610C substitution (FIG. 1). In various configurations, a thiol such as that of a cysteine can be derivatized with a thiol-reactive moiety such as a maleimide moiety of a fluorophore or a fluorescence quencher. In some aspects, prior to derivatization, an oligopeptide of the present teachings can have a single thiol; in various configurations, this thiol can be available for derivatization.

In some aspects, an oligopeptide of the present teachings can comprise, prior to derivatization, at least one amine such as an amino terminal primary amine, or an amino acid comprising a primary amine such as a lysine. An amine of an oligopeptide can be can be available for derivatization with an amine-reactive moiety such as an N-hydroxysuccinimide (NHS) moiety of a fluorophore or a fluorescence quencher. In some aspects, prior to derivatization, an oligopeptide can have a single primary amine that is available for derivatization. In some aspects, an oligopeptide of the present teaching can include a substitution of a lysine of wild type VWF, such as a lysine K1617 for an amino acid that does not comprise a primary amine on its side chain, such as a K1617R substitution (FIG. 1).

In some configurations, an oligopeptide can comprise a substitution of E1598G, which can provide an amino terminal end after release from a precursor. These mutations can result in an oligopeptide having one thiol and one primary amine, which can be available for addition of one fluorophore and one quencher to the oligopeptide (FIG. 1). In various embodiments, these reactive sites can be located on opposite sides of a protease cleavage target site such as the Y-M peptide of von Willebrand Factor. In various configurations, the succinimidyl ester and the maleimide can react through the reactions below, wherein $R^1$ can be a fluorophore or fluorescence quencher and $R^2$ can be an oligopeptide.

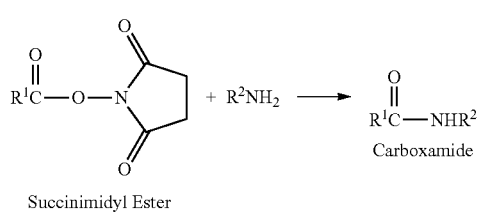

Succinimidyl Ester

Carboxamide

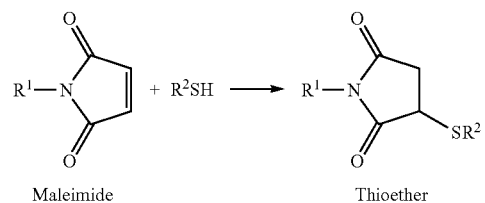

Maleimide

Thioether

Accordingly, as used herein, oligopeptides reacted with such reactive precursors may not include a reactive moiety such as a succinimide in a final product. In various configurations of the present teachings, prior to cleavage of an oligopeptide comprising both a fluorophore and a quencher, fluorescence is quenched. When the Tyr1605-Met1606 bond is cleaved, quenching is relieved, thereby resulting in a fluorescence signal. In various configurations, the fluorescence signal can be proportional to product concentration. In various configurations, a fluorescence signal can be detected by means well known to skilled artisans, such as but not limited to fluorescence spectrometry.

In some configurations, a probe can comprise an oligopeptide consisting of a sequence set forth as SEQ ID NO: 1:

DREQAPNLVYMVTGNPASDEIKRLPGDIQVVPIGVGPNANVQELERIGW
PNAPILIQDFETLPREAPDLVLQR.

In some configurations, a probe can comprise an oligopeptide consisting of a sequence set forth as SEQ ID NO: 2 and as FRETS-rVWF71 (FIG. 1):

GQAPNLVYMVTGCPASDEIRRLPGDIQVVPIGVGPNANVQELERIGWPN
APILIQDFETLPREAPDLVLQR.

In various aspects, a fluorophore can have an absorption maximum of >550 nm or >630 nm. In various aspects, a fluorophore can have an emission maximum of >600 nm or >650 nm. In some aspects, a fluorophore, prior to reaction with an oligopeptide, can be, without limitation, an Alexa Fluor® 594 maleimide (Life Technologies Corp. Carlsbad, Calif.) (abs 590 nm, em 617 nm, ε 96,000) or a DyLight® 633 maleimide (Thermo, abs 638 nm, em 658 nm, ε 170,000).

In various aspects, a quencher can have an absorption maximum of >550 nm or >630 nm. In some aspects, a quencher, prior to reaction with an oligopeptide, can be, without limitation, a QSY21-succinimidyl ester (abs 661 nm, ε 90,000) or an IRDye QC-1 N-hydroxy succinimidyl ester (LI-COR, Lincoln, Nebr.; abs 737 nm, ε 96,000,

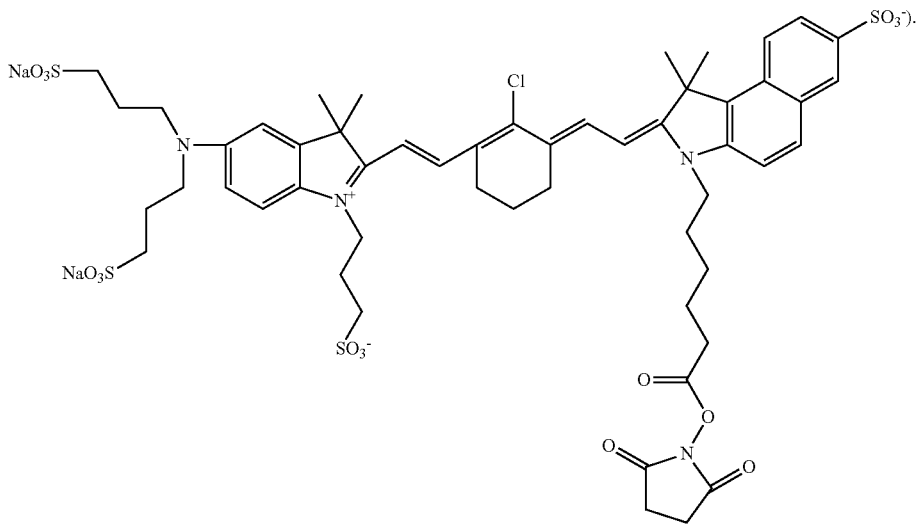

In some aspects, a substrate of the present teachings can comprise a fluorophore or quencher that comprises at least one sulfate. In some aspects, a substrate of the present teachings can be soluble in water at concentrations >50 μM, or greater than that of FRETS-VWF73.

In some embodiments, the present teachings include a vector comprising a nucleic acid sequence encoding an oligopeptide of an ADAMTS13 substrate described herein. In some aspects, a nucleic acid sequence can further encode a His tag such as an N-terminal His tag. In some aspects, a nucleic acid sequence can further comprise a sequence encoding thioredoxin. In some aspects, a nucleic acid sequence can further comprise a sequence encoding a Tobacco Etch Virus (TEV) protease cleavage site. In some aspects, a vector can be a plasmid or a virus, such as a bacteriophage.

In some embodiments, the present teachings include methods of determining presence, absence or quantity of ADAMTS13 activity in a sample. In various configurations, such methods can comprise: forming a mixture comprising a sample and a probe as described herein and measuring fluorescence at one or more time points after forming the mixture.

In some embodiments, the present teachings include methods of determining presence, absence or quantity of ADAMTS13 inhibitor activity in a sample. In various configurations, such methods can comprise: forming a mixture comprising a sample and a probe as described herein and measuring fluorescence at one or more time points after forming the mixture. Such methods can further comprise including in the mixture ADAMTS13 which can be obtained from a source such as, without limitation, ADAMTS13 produced in a microorganism using recombinant methods, or ADAMTS13 present in serum or plasma, such as normal pooled serum or plasma.

In some embodiments, the present teachings include methods of producing a probe described herein. In some configurations, these methods can comprise expressing, in a cell, an oligopeptide encoded by the vector of described herein, digesting the oligopeptide with His-tagged TEV protease to yield an oligopeptide comprising VWF sequence comprising a cysteine as described herein and reacting the cysteine with a fluorophore comprising a maleimide, and reacting a primary amine of the oligopeptide such as the N-terminal primary amine with a fluorescence quencher comprising a succinimidyl ester.

In some embodiments, the present teachings include methods of producing a probe described herein. In some configurations, these methods can comprise expressing, in a cell, an oligopeptide encoded by the vector of described herein, digesting the oligopeptide with His-tagged TEV protease to yield an oligopeptide comprising VWF sequence comprising a cysteine as described herein and reacting the cysteine with a fluorescence quencher comprising a maleimide, and reacting a primary amine of the oligopeptide such as the N-terminal primary amine with a fluorophore comprising a succinimidyl ester or another amine-reactive moiety such as an isothiocyanate.

EXAMPLES

The following Examples are intended to be illustrative of various aspects of the present teachings and are not intended to be limiting of any aspect. While some of examples may include conclusions about the way the invention may function, the inventors do not intend to be bound by those conclusions, but put them forth only as possible explanations. Unless indicated by use of past tense, presentation of an example does not imply that an experiment or procedure was, or was not, conducted, or that results were, or were not, actually obtained.

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Ausubel, F. M., et al., ed., Current Protocols in Molecular Biology, Wiley Interscience, 2003; Nagy, A., et al., Manipulating the Mouse Embryo: A Laboratory Manual (Third Edition), Cold Spring Harbor Laboratory Press, Cold Spring Harbor, N.Y., 2003; Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Graham Solomons T. W., et al., Organic Chemistry 9th edition, Wiley, John & Sons, Incorporated, 2007.

As used herein, the singular forms "a", "an" and "the" are intended to include the plural forms as well, unless the context indicates otherwise. Methods of administration of pharmaceuticals and dosage regimes can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

These and all other publications cited in this disclosure are incorporated herein by reference, each in its entirety.

Example 1

This example illustrates a substrate oligopeptide.

The inventors designed a chimeric construct in plasmid pET-32 Xa/LIC (Novagen, Billerica, Mass.) encoding an N-terminal His-tag, thioredoxin, Tobacco Etch Virus (TEV) protease cleavage site, a Gly residue, and VWF ($Gln^{1599}$-$Arg^{1668}$). Two mutations were made in the VWF segment: N1610C introduced a thiol group for alkylation, and K1617R removed an amino group that competes with the peptide N-terminus for chemical modification. This oligopeptide was expressed in IPTG-induced BL21 cells, purified on Ni-NTA-agarose, and digested with His-tagged TEV protease (made by the present inventors). TEV protease and thioredoxin were removed on Ni-NTA-agarose, and the C-terminal peptide (FIG. 1) was purified by C18 reverse phase HPLC. >100 mg of this peptide was prepared, sufficient for thousands of assays.

In FIG. 1, the scissile Y-M bend is indicated (triangle) and the C-terminal segment of VWF domain A2 which can promote efficient cleavage by ADAMTS13 consists of the carboxy terminal sequence EAPDLVLQR (SEQ ID NO: 6) (underlined), Residues mutated in von Willebrand Disease type 2A, associated with increased proteolysis, are circled. FRETS-rVWF71 has the mutations E1598G, N1610C, and K1617R (boxed). Cys1610 is modified with DyLight 633 and the N-terminus is modified with IRDye QC-1.

Example 2

This example illustrates fluorescence donors and quenchers.

The present inventors have tested several combinations of donor and quencher groups chosen for lack of interference from blood proteins. For example, modification at $Cys^{1610}$ with Alexa Fluor 594 maleimide (abs 590 nm, em 617 nm, $\epsilon$ 96,000) and at N-terminal. Gly with QSY21-succinimidyl ester (abs 661 nm, $\epsilon$ 90,000) gave superior fluorescence quenching and sensitivity compared to FRETS-VWF73, but this substrate had poor solubility. In one embodiment, a substrate of the present teachings is modified at $Cys^{1610}$ with DyLight 633-maleimide (Thermo, abs 638 nm, em 658 nm, $\epsilon$ 170,000), and at N-terminal Gly with IRDye QC-1 N-hydroxysuccinimidyl ester (LI-COR, abs 737 nm, $\epsilon$ 96,000). These dyes incorporate sulfate groups and have markedly increased water solubility. After RP-HPLC purification the doubly-labeled substrate (FRETS-rVWF71) is soluble at >50 µM. These dyes absorb/emit in the near-infrared, which does not overlap with the spectrum of blood proteins, hemoglobin, or bilirubin.

Example 3

This example illustrates ADAMTS13 activity assays.

Preliminary studies show that paired samples of citrated plasma and serum have the same ADAMTS13 activity, which is stable for extended times at 4° C. or −20° C. These findings are consistent with published data (Gerritsen, H. E., et al., Blood. 98:1654-1661, 2001; Furlan, M., et al., Blood. 87:4223-4234, 1996).

Figure 2:
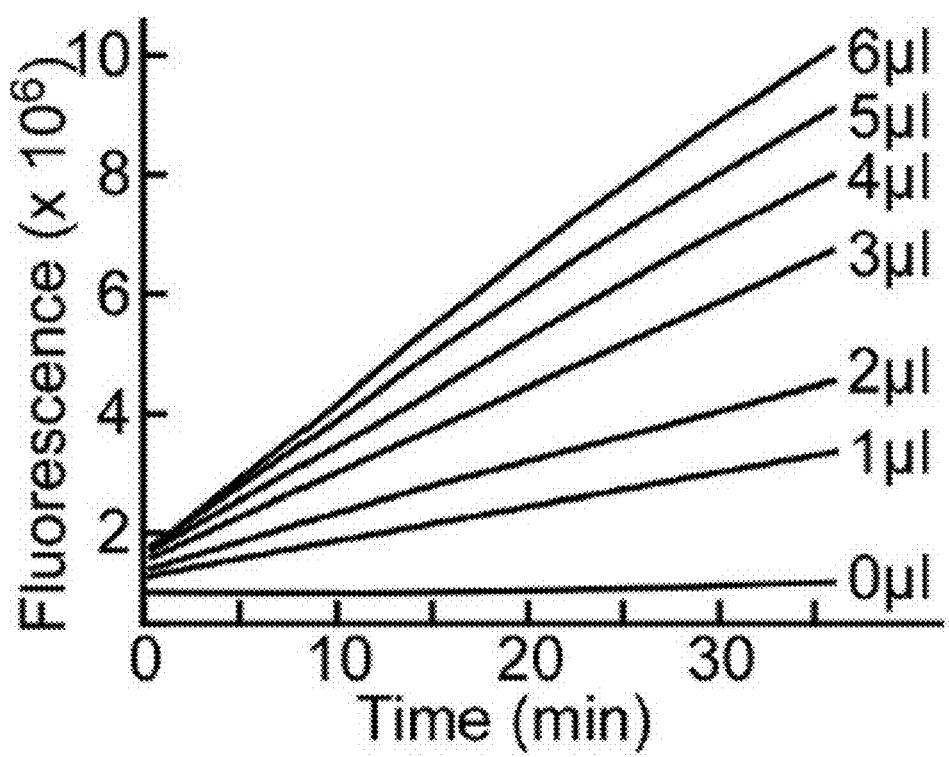
FIG. 2 illustrates FRETS-rVWF71 assays.

In these experiments, the FRETS-rVWF71 substrate was utilized in a microtiter format (FIG. 2), which is compatible with fluorescence plate readers that are supported by laboratory equipment suppliers and available in many clinical hemostasis laboratories, such as the BIO-TEK FLx800 Fluorometer from DiaPharma (West Chester, Ohio) or Technoclone (Vienna). Reactions were performed in 200 µL 5 mM Bis-Tris, pH 6, 25 mM $CaCl_2$, at room temperature with added plasma as shown (FIG. 2). Fluorescence was monitored in a $Victor^2$ V microplate reader (Perkin Elmer Life Sciences, Boston, Mass.) with 638 nm excitation filter and 658 nm emission filter.

Using 1 µM substrate with varying amounts of plasma or serum and optimal filters for each substrate, ΔF/min for VWF-rFRETS71 is 8-fold greater compared to VWF-FRETS73. In addition, assays with VWF-rFRETS71 are linear with time and linear with enzyme up to >95% serum or plasma added, with no significant background fluorescence or interference from blood constituents. The combination of stronger fluorescence signal and compatibility with undiluted plasma make FRETS-rVWF71 ~250-fold more sensitive than FRETS-VWF73.

Example 4

This example illustrates ADAMTS13 inhibitor assays.

In this prophetic example, activity of ADAMTS13 inhibitors is examined. In these experiments, antibody source can be patient serum, optionally heat-treated to inactivate endogenous ADAMTS13 (56° C., 30 min) (Zheng, X. L., et al., Blood. 103:4043-4049, 2004). The ADAMTS13 source is normal pooled serum (or plasma), or recombinant ADAMTS13 to further increase sensitivity. In these assays, a fixed amount of ADAMTS13 (5 µL) and variable amounts of inhibitor (90 µL serum and serial dilutions) are mixed and preincubated (15 min). FRETS-rVWF71 is added (5 µL) and rates of product generation are analyzed by standard methods to yield an inhibitor titer in "Bethesda-like" units. The assay permits the detection of inhibitors at <<0.5 "BU" per mL.

Example 5

This prophetic example illustrates an inhibitor assay based on FRETS-rVWF71 cleavage in minimally diluted $Li^+$-heparin plasma.

We have designed an inhibitor assay based on FRETS-rVWF71 cleavage in minimally diluted $Li^+$-heparin plasma. The inhibitor source is patient plasma, optionally heat-treated to inactivate endogenous ADAMTS13 (56° C., 30 min). Equal amounts of pooled normal plasma and inhibitor (and serial dilutions) are mixed and preincubated. Samples (100µl) are assayed with FRETS-rVWF71 (200 µl final volume) and rates of product generation are analyzed to yield an inhibitor titer in "Bethesda-like" units.

Example 6

This example illustrates ADAMTS13 activity assays.

Figure 7:
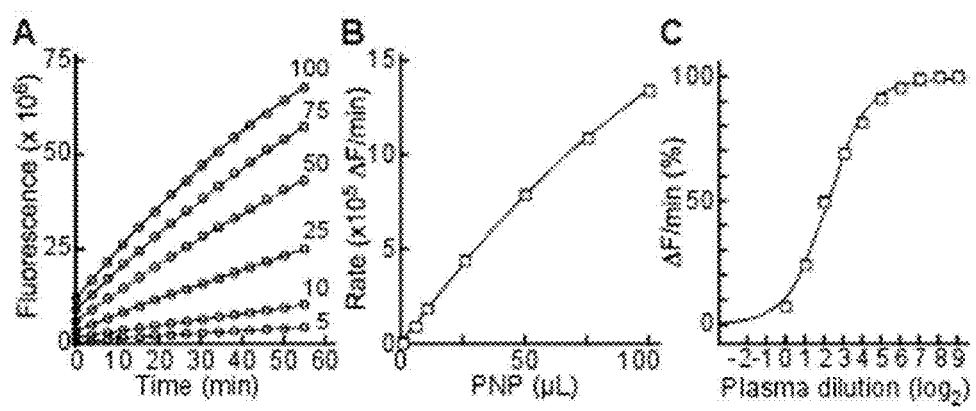
FIG. 7 illustrates plasma concentration dependence of FRETS-rVWF71 assays.

In these experiments (FIG. 7A), reactions were performed in 200 µL 50 mM HEPES, pH 7.4, 150 mM NaCl, 10 mM $CaCl_2$, 100 µg/ml BSA, 0.05% Tween 20, at 30° C. with added plasma, in a Perkin Elmer Victor2V plate reader with 635/15 nm excitation and 660/10 nm emission filters. FIG. 7B shows initial slope vs. PNP standard curve.

After RP-HPLC purification, the doubly-labeled substrate "FRETS-rVWF71" is soluble at >200 µM. In addition, assays with FRETS-rVWF71 were insensitive to >20 mg/dL (250

μM) conjugated bilirubin, which is incompatible with FRETS-VWF73 (Meyer, S. C., et al., J. Thromb. Haemost. 5: 866-867, 2007).

In these experiments, samples were analyzed from 100 healthy controls. The mean ADAMTS13 activity was 1.11 U/mL with SD 0.21 U/dL (referenced to local pooled normal plasma). Intra-assay and inter-assay coefficients of variation were <3%. Results obtained with FRETS-rVWF71 and FRETS-VWF73 were congruent, with a coefficient of variation of 3.8% for healthy controls assayed by both methods.

Example 7

This example illustrates preparation of fluorogenic FRETS-rVWF71 substrate.

In these experiments, a precursor substrate peptide was expressed from a plasmid that encodes thioredoxin, a His-tag, a TEV cleavage site, and VWF $Gln^{1599}$-$Arg^{1668}$. The mutation D1610C introduced a unique Cys, and the mutation K1617R removed a primary amine that otherwise would have competed with subsequent chemical modification of the N-terminus. The expressed chimeric protein was readily soluble and was purified by chromatography on Ni-NTA agarose (FIG. 3) with a yield of >50 mg/L of LB culture medium. Removal of thioredoxin by cleavage with His-tagged TEV protease gave the product rVWF71, which has an extra Gly before VWF residues $Gln^{1599}$-$Arg^{1668}$. Peptide rVWF71 was purified by Ni-NTA chromatography to remove His-tagged thioredoxin and TEV protease, followed by reverse-phase HPLC (FIG. 3) to yield >10 mg rVWF71/L of LB culture medium.

FIG. 3A shows polyacrylamide 4-12% gel electrophoresis of intermediates and purified FRETS-rVWF71. Lanes correspond to: 1, protein markers; 2, thioredoxin-VWF71 fusion protein eluted from Ni-NTA agarose; 3, after cleavage by TEV protease; 4, unbound products after rechromatography on Ni-NTA agarose; 5, after purification by HPLC; 6, rVWF71 peptide modified with DyLight 633 and purified by HPLC; 7, purified FRETS-rVWF71; 8, purified FRETS-rVWF71. Except for lanes 6 and 7, which are unstained, gels were stained with Simply Blue SafeStain.

FIG. 3B shows purification of rVWF71 peptide. In these experiments, thioredoxin-VWF71 fusion protein was digested with TEV protease, chromatographed on Ni-NTA agarose to remove His-tagged TEV protease and thioredoxin, and purified by HPLC on a C18 column in 0.1% TFA developed with a 20-90% acetonitrile gradient. The eluate was monitored for absorbance at 280 nm. The peak at 20 min corresponds to panel A, lane 5.

FIG. 3C shows purification of singly modified rVWF71. In these experiments, DyLight 633-rVWF71 was purified by HPLC on a C18 column in 50 mM TEAA, pH 6.0, developed with a 20-45% acetonitrile gradient. The eluate was monitored for absorbance at 280 nm and 627 nm, and for emission at 658 nm after excitation at 635 nm. The inset shows an expanded view of the peak at 23 min with traces labeled by wavelength.

FIG. 3D shows purification of FRETS-rVWF71. In these experiments, after reaction with IRDye QC-1 N-hydroxy-succinimidyl ester, FRETS-rVWF71 was purified by HPLC as described for DyLight 633-rVWF71 (panel C) with additional monitoring of absorbance at 819 nm. The inset shows an expanded view of the peak at 21 min with traces labeled by wavelength.

In these experiments, DyLight 633 maleimide (Thermo Scientific, Waltham, Mass.) 1 mg/100 μL in dimethyl sulfoxide (DMSO) was added dropwise with stirring to peptide VWF71 (10 mg) in ≤2 mL of 100 mM sodium phosphate, pH 7.1, in the dark, and stirred overnight at room temperature. The product DyLight 633-rVWF71 was purified by HPLC on C18 using the TEAA/acetonitrile solvent system as described for the purification of VWF71. DyLight 633-rVWF71 was lyophilized and desalted on a small column of PD-10 in ≤2 mL of 100 mM sodium phosphate, pH 7.9. IRDye QC-1 N-hydroxysuccinimide ester 0.5 mg in 100 μL DMSO was added dropwise with stirring and the solution was stirred overnight at room temperature protected from light. The product FRETS-rVWF71 was purified by reverse phase HPLC, lyophilized, dissolved in ≤0.5 mL of deionized water and applied onto a column (7×230 mm) of Amberlite IR120 sodium form. FRETS-rVWF71 product was eluted with deionized water and lyophilized or concentrated by ultrafiltration to ≥250 μM. The concentration was verified by amino acid analysis (The Protein Chemistry Laboratory, Texas A&M University). Working stocks stored at −20° C. were thawed and refrozen repeatedly over several months without any change in stability or chemical properties.

Figure 3:
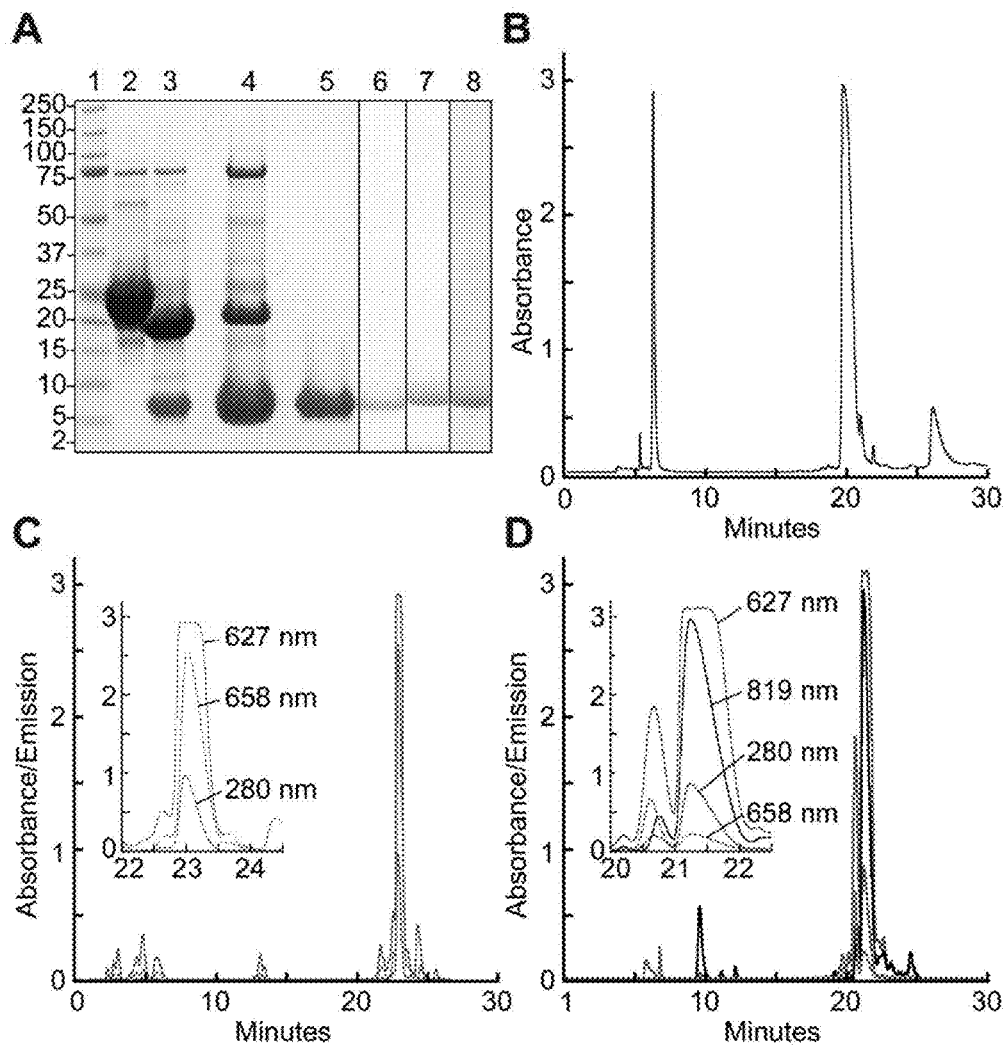
FIG. 3 illustrates preparation of FRETS-rVWF71.

The rVWF71 was modified with DyLight 633 maleimide in ~70% yield and purified by HPLC (FIG. 3). The rVWF71 had been reduced with 10 mM dithiothreitol before purification by HPLC and buffer exchange to maximize the efficiency of alkylation by DyLight 633 maleimide. The N-terminal Gly of DyLight 633-rVWF71 was modified with IRDye QC-1 N-hydroxy-succinimidyl ester in ~90% yield and purified by HPLC. The final FRETS-rVWF71 product was converted into the sodium salt, which was stable and soluble at >250 μM.

Absorbance maxima for FRETS-rVWF71 were observed at 627 nm and 819 nm, consistent with the presence of both dyes. Upon excitation at 635 nm, the fluorescence emission at 660 nm of uncleaved FRETS-rVWF71 and fully cleaved FRETS-rVWF71 showed little dependence on pH, varying <7% between pH 5 and pH 10.

Example 8

This example illustrates the optimization of FRET-rVW71 cleavage by plasma ADAMTS13.

In these experiments, matched samples of serum, and plasma anticoagulated with sodium citrate, $Li^+$-heparin and $Na^+$-heparin were obtained from volunteer healthy donors with informed consent according to a human studies protocol approved by the Washington University Institutional Review Board.

Assays were performed at 30° C. Samples (100 μL) of plasma or serum, diluted as necessary in assay buffer, were pipetted in duplicate in 96 well white microplates (Optiplate-96, PerkinElmer, Waltham, Mass.). Reaction was initiated by addition of 100 μL substrate in assay buffer. Cleavage of FRETS-rVWF71 was detected as an increase in fluorescence compared to control reactions without added enzyme at 2 min intervals using a Victor$^2$V Multilabel Counter (PerkinElmer, Waltham, Mass.) or Synergy H1 Hybrid Multi-Mode Microplate Reader (Biotek, Winooski, Vt.) equipped with 635±10 nm excitation and 660±10 nm emission filters. Initial velocities were determined by fitting progress curves to the polynomial $\Delta F = A + Bt + Ct^2$, where $\Delta F$ is the change in fluorescence, t is time, A is the y-intercept, B is the initial velocity (slope), and the term $Ct^2$ accounts for any decline in velocity due to substrate consumption or photobleaching.

ADAMTS13 assays with the FRETS-VWF73 substrate (Kokame, K., et al. Br. J. Haemotol. 129:93-100, 2005) (Peptide International, Louisville, Ky.) were performed according to the manufacturer's instructions. Hemoglobin was prepared by hypotonic lysis of red blood cells from a voluntary donor and quantified with Drabkin's reagent (Sigma, St. Louis, Mo.).

Figure 4:
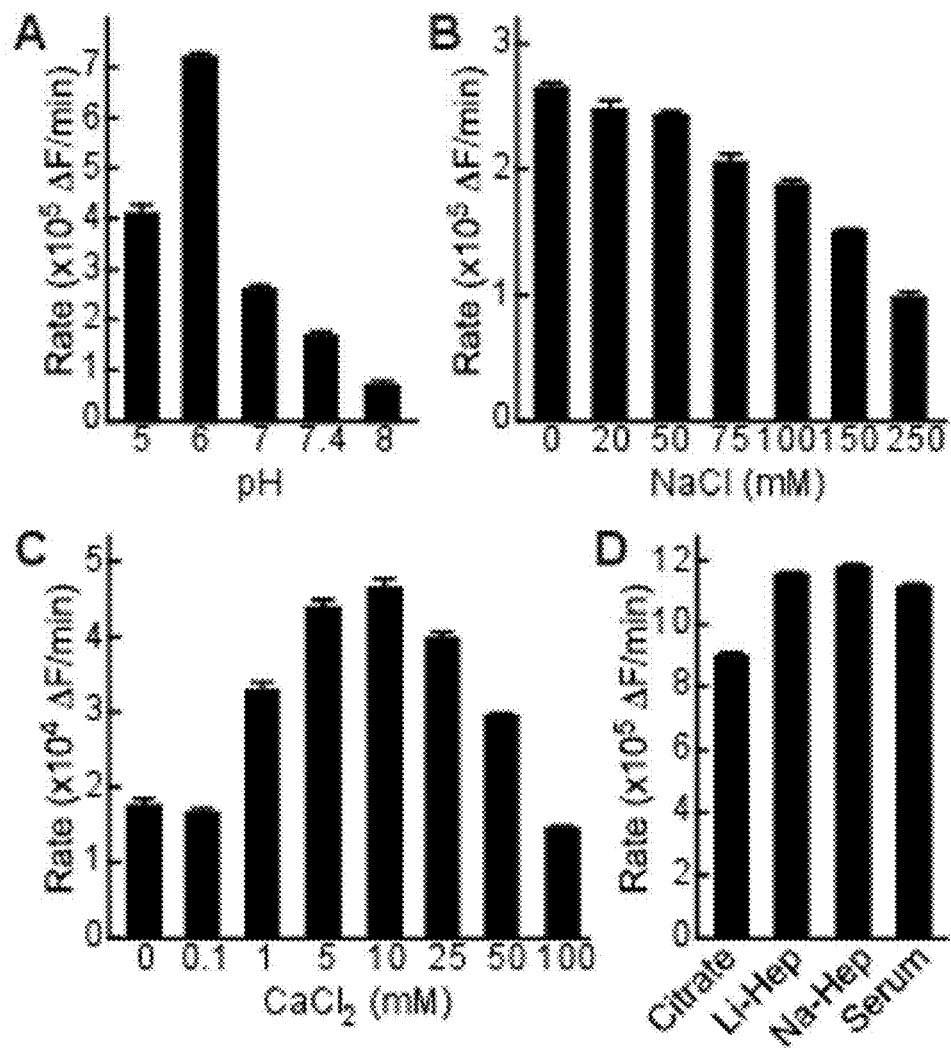
FIG. 4 illustrates ADAMTS13 activity toward FRETS-rVWF71.

Optimal conditions for cleavage of FRETS-rVWF71 were similar to those reported for ADAMTS13 cleavage of other substrates (Kokame, K., et al. Br. J. Haemotol. 129:93-100, 2005; Tsai, H. M., et al. Blood. 87:4235-44, 1996; Anderson, P. J., et al. J. Biol. Chem. 281:850-7, 2006). Activity was maximal at pH 6, very low ionic strength, and 5-10 mM $CaCl_2$ (FIG. 4). Under conditions of physiological ionic strength (150 mM NaCl) and pH 7.4, the rate of reaction was decreased ~50%.

To optimize compatibility with minimally diluted plasma samples, the standard assay buffer was made 50 mM HEPES, pH 7.4, 150 mM NaCl, and 10 mM $CaCl_2$, supplemented with 0.05% Tween-20 and 400 µg/mL bovine serum albumin. Under these conditions, assays of serum or plasma anticoagulated with citrate, Li+-heparin or Na+-heparin gave comparable results. Values for citrated plasma were decreased as expected from dilution by the citrate anticoagulant solution (FIG. 4). Li+-heparin plasma is commonly used for clinical chemistry assays and therefore was selected for ADAMTS13 assay development.

Figure 5:
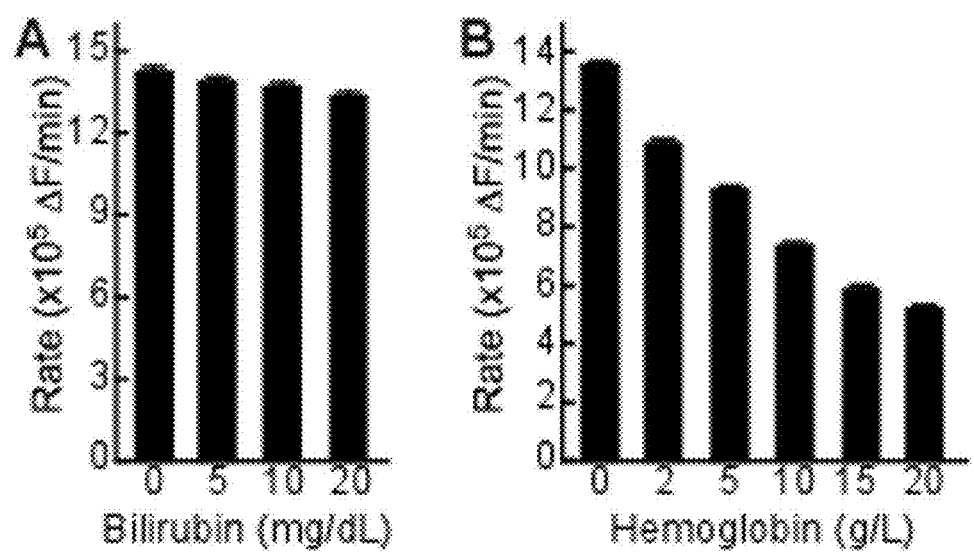
FIG. 5 illustrates effect of bilirubin and hemoglobin on FRETS-rVWF71.

Bilirubin interferes with ADAMTS13 assays that use the FRETS-VWF73 substrate because bilirubin absorbs light at the same wavelengths as the chromophores in the substrate (Hovinga, J. A. K., et al. J. Thromb. Haemost. 5:866-7, 2007). However, the spectrum of bilirubin does not overlap with DyLight 633 and IRDye QC-1, and bilirubin ≤20 mg/dL did not inhibit ADAMTS13 activity assays with FRETS-rVWF71 (FIG. 5). Hemoglobin absorbs at 550 nm and also interferes with FRETS-VWF73 assays. In addition, hemoglobin directly inhibits ADAMTS13 regardless of the assay method (Studt, J. D., et al. Blood. 105:542-4, 2005). As expected, hemoglobin ≤20 g/L) did not affect the detection of FRETS-rVWF71 cleavage products, but did inhibit ADAMTS13 activity with an IC50 of 10-15 g/L (FIG. 5).

Example 9

This example illustrates the kinetics of FRETS-rVWF71 cleavage.

In these experiments, FRETS-rVWF71 cleavage by plasma ADAMTS13 (50 µL) was assessed in 200 µL reactions containing 50 mM HEPES, pH 7.4, 10 mM $CaCl_2$, 150 mM NaCl, and 0.05% Tween-20, and varying concentrations of FRETS-rVWF71. The concentration of ADAMTS13 in PNP is ~1.03 µg/ml (Feys, H. B., et al. J. Thromb. Haemost 4:955-62, 2006), or ~6 nM for a molecular mass of 170 kDa. For each concentration of substrate, the relationship between product fluorescence and concentration was determined directly by cleaving FRETS-rVWF71 to completion with excess recombinant ADAMTS13 MDTCS (Feys, H. B., et al. J. Thromb. Haemost. 7:2088-95, 2009) and measuring the fluorescence. Control assays contained plasma that was completely deficient in ADAMTS13. The initial velocities (nM/min) as a function of substrate concentration were fitted to the Michealis-Menten equation by nonlinear regression analysis (Prism, GraphPad).

Figure 6:
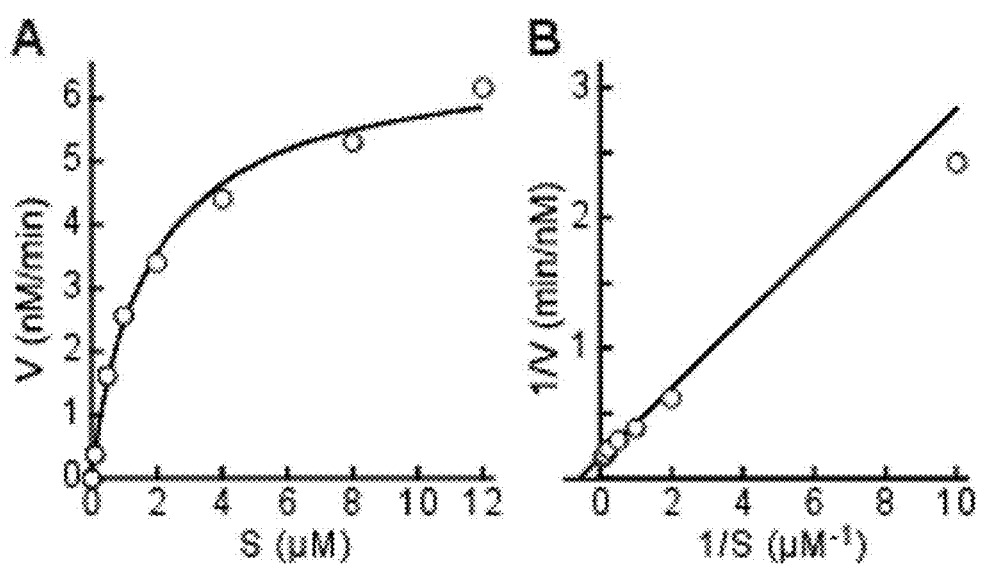
FIG. 6 illustrates kinetics of FRETS-rVWF71 cleavage by plasma ADAMST13.

Plasma ADAMTS13 cleaved FRETS-rVWF71 with a $K_m$ of 1.8 µM and a $k_{cat}$ of 6.8 min$^{-1}$ at 30° C. (FIG. 6). For comparison, ADAMTS13 cleaves FRETS-VWF73 in the same buffer with a $K_m$ of 3.2 µM and a $k_{cat}$ of 58 min$^{-1}$ at 37° C. (Anderson, P. J., et al. J. Biol. Chem. 281:850-7, 2006). Therefore, the larger dyes of FRETS-rVWF71 do not impair substrate binding to ADAMTS13 but decrease the rate of catalysis ~8-fold.

Example 10

This example demonstrates FRETS-rVWF71 assay performance.

Progress curves for cleavage of FRETS-rVWF71 by plasma ADAMTS13 were approximately linear with time for at least 60 minutes (FIG. 7A). To account for small time-dependent decreases in reaction rate with high concentrations of enzyme, initial rates were obtained by fitting to a second order polynomial. Reaction rate increased approximately linearly with the volume of added plasma. For maximum sensitivity reactions were performed with 100 µL plasma in a reaction volume of 200 µL. Standard calibration curves were constructed with PNP (FIG. 7B).

Results with FRETS-rVWF71 and FRETS-VWF73 assayed under standard conditions (Kokame, K., et al. Br. J. Haematol. 129:93-100, 2005) correlated well with an inter-assay CV of 3.8%. Using 1 µM substrate and 5 µL PNP, the change in fluorescence (ΔF/min) for FRETS-rVWF71 (50 mM HEPES, pH 7.4, 150 mM NaCl) was 8-fold greater than for FRETS-VWF73 (5 mM Bis-Tris, pH 6).

The FRETS-rVWF71 assay for ADAMTS13 activity has been adapted to measure autoantibody inhibitors of ADAMTS13 in a manner analogous to the measurement of factor VIII inhibitors in "Bethesda-like" units.

Plasma samples with ADAMTS13 protease activity <10% were tested for the presence of an ADAMTS13 inhibitor. Plasma samples were serially diluted two-fold with assay buffer (50 mM HEPES, pH 7.4, 150 mM NaCl, 10 mM $CaCl_2$, and 0.05% Tween-20) to yield 8 dilutions. In duplicate, PNP (50 µL) was mixed with an equal volume (50 µL) of undiluted test plasma and each serially diluted sample. Control conditions included PNP mixed with an equal volume of cleavage buffer. The microplate containing the samples was sealed with adhesive film (Sealplate, Excel Scientific, Victorville, Calif.) and incubated at 37° C. for 1 h. Reaction was initiated by addition of 100 µL of assay buffer containing 2 µM FRETS-rVWF71. Fluorescence emission was monitored and initial reaction rates were determined.

The inhibitor titer was determined by fitting the initial reaction rates to a four parameter logistic model or sigmoidal dose response equation by nonlinear regression (Prism):

$$\text{Rate}(D)=\text{Max}+(\text{Max}-\text{Min})/(1+10^{\wedge}((\log T - \log D)*H))$$

Where Rate(D) is the initial rate with test plasma at dilution D, Max is the maximum rate in the absence of test plasma, Min is the rate with no active enzyme (fixed at 0), H is the Hill slope, and T is the inhibitor titer.

For selected patient samples, ADAMST13 activity and inhibitor titer were measured with FRETS-VWF73 at the BloodCenter of Wisconsin reference laboratory.

A fixed amount of ADAMTS13 in PNP (100 µL) was preincubated with serially diluted plasma samples and assayed for ADAMTS13 activity. Reaction rates were analyzed according to a model for competitive sigmoidal dose-response inhibition to obtain the dilution of plasma at which ADAMTS13 activity is decreased by 50%, and the inverse of the dilution is the inhibitor titer (FIG. 7C). This assay design allows the detection of inhibitors with a titer <0.5 U/ml.

Example 11

This example illustrates ADAMTS13 assays in healthy donors and patients with TTP.

In these experiments, frozen Li$^+$-heparin plasma samples were obtained from 100 healthy controls (Biological Specialty Corp., Colmar, Pa.) deidentified except for demographic information on gender, age, and ethnicity. Pooled normal Li$^+$-heparin plasma (PNP) for assay standardization was prepared from at least 35 donors. For each healthy control, 25 µL and 100 µL plasma samples were assayed in duplicate for ADAMST13 activity. Up to 20 healthy controls were assayed per 96 well microplate. For cross-validation, ≥3 samples were randomly selected from each assayed batch and reanalyzed with the subsequent batch. A standard curve was constructed from duplicate assays of PNP 5 µL, 25 µL, 50 µL, 75 µL and 100 µL. ADAMST13 activity of randomly selected controls samples was determined by the FRETS-VWF73 method.

Li+-heparin plasma was obtained from individuals suspected to have TPP with their informed consent according to a human studies protocol approved by the Washington University Institutional Review Board. Anticoagulated blood was centrifuged at 2000×g for 10 min at 10° C., and the blood cells debris were discarded. The supernatant was assayed immediately and the remainder stored in aliquots at −80° C.

Figure 8:
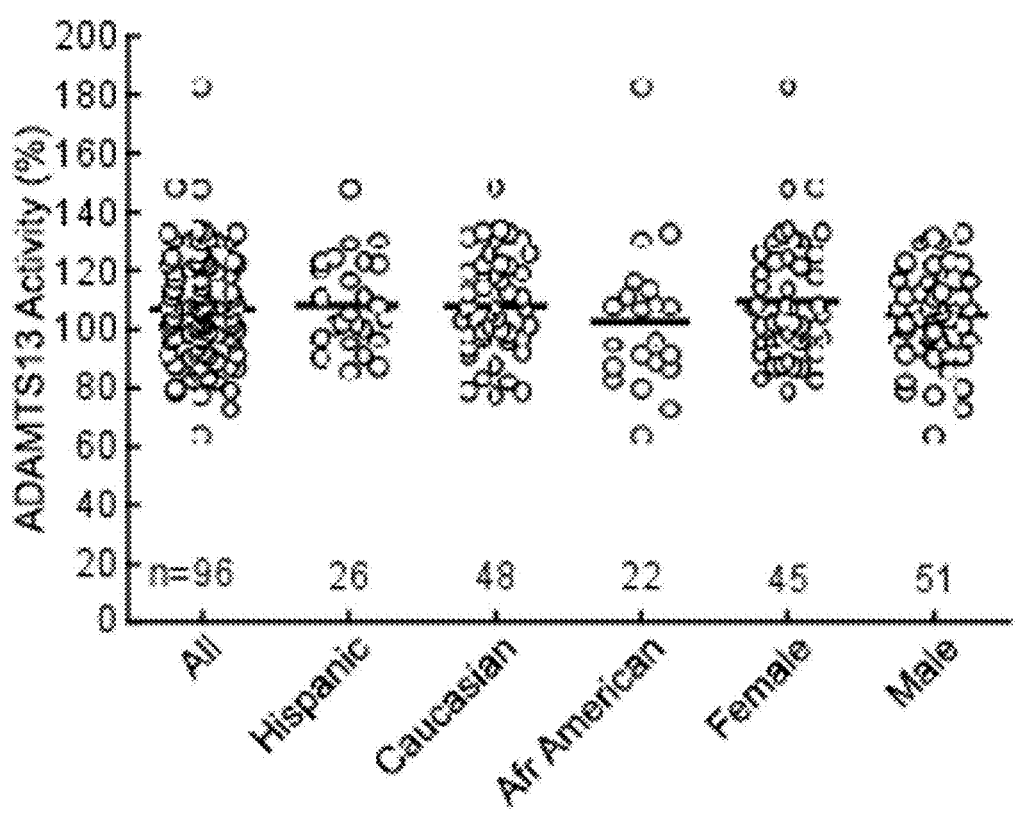
FIG. 8 illustrates plasma ADAMTS13 activity of healthy controls.

ADAMST13 activity was assayed in Li+-heparin plasmas from 96 healthy controls (FIG. 8). Using a PNP standard prepared from 35 donors, the mean ADAMTS13 activity was 107±18% (SD). Intra-assay and inter-assay coefficients of variation were less <2%. Mean ADAMTS13 activity was not significantly different based on gender or ethnicity (FIG. 8). There was no significant relationship between ADAMTS13 activity and age.

ADAMTS13 assays using both FRETS-rVWF71 and FRETS-VWF73 substrates were performed on samples from several patients with idiopathic TTP (Table 1). Both substrates gave consistent results for ADAMTS13 activity, although FRETS-rVWF71 assays were 20-fold more sensitive. Three patients did not have detectable ADAMTS13 inhibitors by either assay. For the remaining patients, inhibitor assays with FRETS-rVWF71 gave titers 1.4-fold to >5-fold higher than inhibitor assays with FRETS-VWF73. This difference in sensitivity for inhibitors reflects the 1:20 dilution of plasma required for assays with FRETS-VWF73.

TABLE 1

Comparison of ADAMTS13 assays for patients with TTP

| Patient | ADAMTS13 activity (%) | | ADAMTS13 Inhibitor (units/ml) | |
|---|---|---|---|---|
| | FRETS-rVWF71 | FRETS-VWF73 | FRETS-rVWF71 | FRETS-VWF73 |
| UPN 323 | 7.6 | <5 | 3.8 | 1.0 |
| UPN 330 | 1.8 | <5 | 4.5 | 1.8 |
| UPN 333 | 2.2 | <5 | 1.9 | 0.9 |
| UPN 334 | 0.2$^a$ | <5$^b$ | 23$^a$ | 3.6$^b$ |
| UPN 335 | 10 | <5 | <0.4 | <0.4 |
| UPN 336 | 1.8 | <5 | 3.1 | 0.6 |
| UPN 337 | 1.2 | <5 | <0.4 | <0.4 |
| UPN 339 | 30 | 14 | <0.4 | <0.4 |
| UPN 340 | 1.9 | <5 | <0.4 | 1.8 |
| UPN 342 | 9.5 | 7 | 2.7 | 1.9 |
| UPN 346 | 3.3 | <5 | ND | ND |

$^a$Sample of Sep. 5, 2011.
$^b$Sample of Sep. 13, 2011.
ND, not done.

Example 12

This example illustrates construction of a vector of the present teachings.

To construct a plasmid comprising a sequence encoding amino acid residues Gln1599-Arg1668 (VWF70) of von Willebrand factor (VWF), DNA sequence of VWF was amplified from pSVHvWF1 (Matsushita, T., and Sadler, J. E. J. Biol. Chem. 270:13406-14, 1995) using primers with Ligation Independent Cloning overhangs (Aslanidis, C. and de Jong, P. J. Nucleic. Acids. Res. 18:6069-74, 1990):

Forward,
(SEQ ID NO: 4)
GGTAATGAGGGTCGCGAGAACCTTTATTTCCAGGGCCAGGCGCCC

Reverse,
(SEQ ID NO: 5)
AGAGGAGAGTTAGAGCCTCACCTCTGCAGCACCAGGTC

The forward primer encodes a tobacco etch virus (TEV) protease cleavage site and the reverse primer introduces a stop codon. The PCR product was purified and ligated into pET-32 Xa/LIC (Novagen, Billerica, Mass.) to yield a plasmid that encodes thioredoxin, a His-tag, a TEV cleavage site, a Gly residue, and VWF Gln1599-Arg1668. The mutations D1610C and K1617R were introduced using a site-directed mutagenesis kit (Stratagene, Santa Clara, Calif.) to yield plasmid pET32XaTEVvWF70. The sequence was confirmed by ABI BigDye V3.1 terminator cycle sequencing.

Example 13

This example illustrates recombinant peptide preparation.

In these experiments, plasmid pET32XaTEVvWF70 was transformed into E. coli BL21 (DE3). Single colonies were inoculated in 5 mL of LB medium containing 50 µg/mL ampicillin and grown for 5 h at 37° C. with shaking at 250 rpm. While maintaining the antibiotic and growth conditions, the 5 mL culture was transferred into 50 mL of LB for 1 h, after which the 50 mL culture was transferred into 1 L of LB. When the culture reached optical density at 600 nm of ~0.6-0.7, isopropyl β-D-1-thiogalactopyranoside (IPTG) was added to 1 mM and incubation was continued for 4 hours. The cell pellet was obtained by centrifugation at 8,000×g for 15 min at 4° C. and stored at −80° C. if not processed immediately.

The cell pellet was thawed in water at room temperature for 10 min and resuspended in 10 mL/g pellet of B-PER Protein Extraction Reagent (Pierce), 10 µL/mL benzonase (Sigma, St. Louis, Mo.) 10 µL/mL, Halt Protease Inhibitor Cocktail (Pierce) and 1 mM phenylmethylsulfonyl fluoride. The suspension was incubated for 15 min at room temperature with gentle shaking (Orbitron Rotator I, Boekel Scientific). The supernatant was recovered by centrifugation at 20,000×g for 15 min at 4° C., diluted with an equal volume of His-binding buffer (20 mM sodium phosphate, pH 7.4, 500 mM NaCl, and 10 mM imidazole), and applied to a 5 ml column of nickel-nitrilotriacetic acid (Ni-NTA) agarose beads (Agarose Beads Technologies, Spain) equilibrated with His-binding buffer. The Ni-NTA column was washed with 50 mL of His-binding buffer and bound protein was eluted with 300 mM imidazole in His-binding buffer. The eluted protein was concentrated to 10 mL by ultrafiltration and dialyzed in a Slide-A-Lyzer cassette (MWCO 7,000, Pierce) overnight with two buffer changes against TEV protease cleavage buffer (50 mM Tris-HCl, pH 8.0, 1 mM dithiothreitol, and 0.5 mM EDTA).

The protein concentration was determined by the BCA method (BioRad, Hercules, Calif.) and the affinity tags cleaved by adding 1 mg of His-tagged TEV protease (Kapust, R. B. and Waugh, D. S. Protein. Sci. 8:1668-74, 1999) per 10 mg of protein and incubation for 16-20 h at room temperature. The solution was dialyzed overnight against His-binding buffer in a Slide-A-Lyzer cassette (MWCO 3,000), and cleaved affinity tags and TEV protease were removed by adsorption on Ni-NTA agarose. Dithiothreitol was added to 10 mM and the unbound product was further purified by HPLC on a C18 column (300 Å, 5 µm, 150×10 mm, GraceVydac) equilibrated with buffer A (50 mM triethylammonium acetate (TEAA), pH 6.0) and developed at 2 mL/min with 3 min of 35% buffer B (60% acetonitrile/40% 50 mM TEAA, pH 6.0) followed by a linear gradient of 35%-75% buffer B for 35 min. Alternatively, the column was equilibrated with 0.1% trifluoroacetic acid (TFA) and developed at 2 mL/min with 20% buffer C (0.092% TFA, 90% acetonitrile) for 5 min, followed by a linear gradient of 20% to 90% buffer C for 35 min. Fractions containing pure VWF71 peptide were lyophilized using a Speed Vac concentrator (Savant), dissolved in a minimum volume of 100 mM sodium phosphate, pH 7.1, and desalted on a small column of PD-10 in the same buffer.

---

What is claimed is:

1. A probe comprising:
   an oligopeptide consisting of no more than 80 amino acids of sequence of von Willebrand Factor (VWF), said oligopeptide comprising a scissile Y1605-M1606 peptide of a VWF sequence set forth as SEQ ID NO: 3, a cysteine substitution located from 1 to 12 amino acids from the scissile Y-M in the carboxy terminal direction, and a C-terminal segment;
   a fluorophore: and
   a fluorescence quencher,
   wherein the fluorophore and the fluorescence quencher are bound to the oligopeptide on opposite sides of the scissile Y-M peptide and wherein the oligopeptide comprises a substitution of lysine K1617 of a VWF sequence set forth as SEQ ID NO: 3 with an amino acid that does not comprise a primary amine on its side chain.

2. A probe in accordance with claim 1, wherein the cysteine substitution is a substitution of an amino acid located at least 3 amino acids from the scissile Y-M peptide.

3. A probe in accordance with claim 1, wherein the cysteine substitution is a N1610C substitution of a VWF sequence set forth as SEQ ID NO: 3.

4. A probe in accordance with claim 1 wherein the oligopeptide consists of the sequence set forth as SEQ ID NO: 2.

5. A probe in accordance with claim 1. wherein the fluorophore has an absorption maximum >550 nm.

6. A probe in accordance with claim 1, wherein the fluorophore has an emission maximum >600 nm.

7. A probe in accordance with claim 1 wherein the fluorophore is selected from the group consisting of Alexa Fluor®594 maleimide (fluorophore)

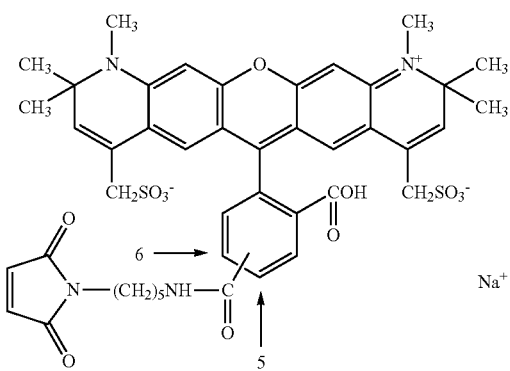

and DyLight®633 maleimide (fluorophore)

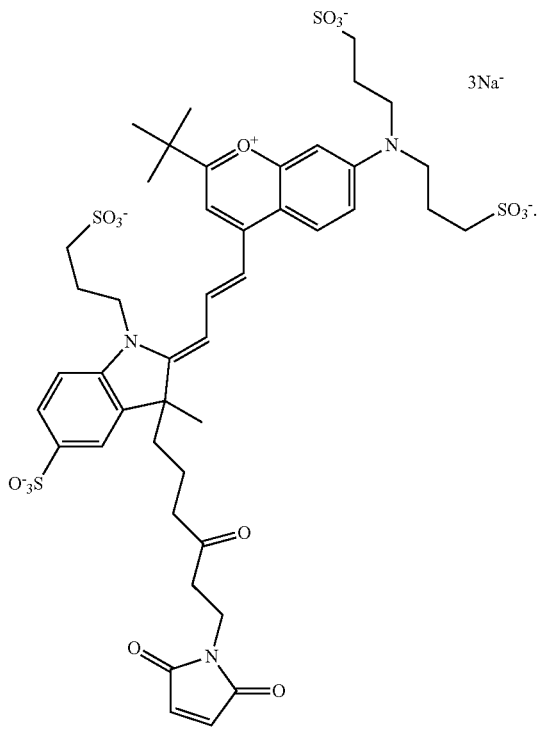

8. A probe in accordance with claim 1 wherein the quencher has an absorption maximum >550 nm.

9. A probe in accordance with claim 1, wherein at least one of the fluorophore and the quencher comprises at least one sulfate.

10. A probe in accordance with claim 1, wherein the quencher is selected from the group consisting of QSY® (fluorescence quencher) 21- succinimidyl ester and IRDye® (infrared dye) QC-1 N-hydroxy succinimidyl ester.

11. A probe in accordance with claim 1, wherein the probe is soluble in water at >50 μM.

12. A method of determining presence, absence or quantity of ADAMTS13 activity in a sample, comprising;
   forming a mixture comprising a sample and a probe of claim 1; and
   measuring fluorescence at one or more time points after forming the mixture, wherein the sample is diluted less than 20-fold.

13. A method in accordance with claim 12, wherein the sample is selected from the group consisting of a serum sample, an undiluted serum sample, a concentrated serum sample, a plasma sample, an undiluted plasma sample and a concentrated plasma sample.

14. A method of determining presence, absence or quantity of ADAMTS13 inhibitor activity in a sample, comprising;
  forming a mixture comprising a sample, as source of ADAMTS13, and a probe of claim 1; and
  measuring fluorescence at one or more time points after forming the mixture.

15. A method in accordance with claim 14, further comprising inactivating ADAMTS13 activity endogenous to the sample prior to forming the mixture.

16. A method in accordance with claim 14, wherein the source of ADAMTS13 is selected from the group consisting of normal plasma, recombinant ADAMTS13 and a combination thereof.

17. A method in accordance with claim 14, wherein the sample is selected from the group consisting of a serum sample, an undiluted serum sample, a concentrated serum sample, a plasma sample, an undiluted plasma sample and a concentrated plasma sample.

18. A probe in accordance with claim 1, wherein the C-terminal segment consists of sequence EAPDLVLQR(SEQ ID NO: 6).

19. A probe comprising:
  an oligopeptide consisting of no more than 80 amino acids of sequence of von Willebrand Factor (VWF), said oligopeptide comprising a scissile Y-M peptide, a cysteine substitution located from 1 to 12 amino acids from the scissile Y-M in the carboxy terminal direction, and a C-terminal segment;
  as fluorophore; and
  as fluorescence quencher,
wherein the fluorophore and the fluorescence quencher are bound to the oligopeptide on opposite sides of the scissile Y-M peptide and wherein the oligopeptide consists of the sequence set forth as SEQ ID NO: 2.

* * * * *

SEQUENCE LISTING

<160> NUMBER OF SEQ ID NOS: 6

<210> SEQ ID NO 1
<211> LENGTH: 73
<212> TYPE: PRT
<213> ORGANISM: Homo sapiens

<400> SEQUENCE: 1

Asp Arg Glu Gln Ala Pro Asn Leu Val Tyr Met Val Thr Gly Cys Pro
1               5                   10                  15

Ala Ser Asp Glu Ile Lys Arg Leu Pro Gly Asp Ile Gln Val Val Pro
                20                  25                  30

Ile Gly Val Gly Pro Asn Ala Asn Val Gln Glu Leu Glu Arg Ile Gly
            35                  40                  45

Trp Pro Asn Ala Pro Ile Leu Ile Gln Asp Phe Glu Thr Leu Pro Arg
        50                  55                  60

Glu Ala Pro Asp Leu Val Leu Gln Arg
65                  70

<210> SEQ ID NO 2
<211> LENGTH: 71
<212> TYPE: PRT
<213> ORGANISM: Homo sapiens

<400> SEQUENCE: 2

Gly Gln Ala Pro Asn Leu Val Tyr Met Val Thr Gly Cys Pro Ala Ser
1               5                   10                  15

Asp Glu Ile Arg Arg Leu Pro Gly Asp Ile Gln Val Val Pro Ile Gly
                20                  25                  30

Val Gly Pro Asn Ala Asn Val Gln Glu Leu Glu Arg Ile Gly Trp Pro
            35                  40                  45

Asn Ala Pro Ile Leu Ile Gln Asp Phe Glu Thr Leu Pro Arg Glu Ala
        50                  55                  60

Pro Asp Leu Val Leu Gln Arg
65                  70

<210> SEQ ID NO 3
<211> LENGTH: 2813
<212> TYPE: PRT
<213> ORGANISM: Homo sapiens

<400> SEQUENCE: 3

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

-continued

```
Arg Val Ser Leu Ser Val Tyr Leu Gly Glu Phe Phe Asp Ile His Leu
                85                  90                  95
Phe Val Asn Gly Thr Val Thr Gln Gly Asp Gln Arg Val Ser Met Pro
            100                 105                 110
Tyr Ala Ser Lys Gly Leu Tyr Leu Glu Thr Glu Ala Gly Tyr Tyr Lys
            115                 120                 125
Leu Ser Gly Glu Ala Tyr Gly Phe Val Ala Arg Ile Asp Gly Ser Gly
        130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Met Thr Gln
                165                 170                 175
Glu Gly Thr Leu Thr Ser Asp Pro Tyr Asp Phe Ala Asn Ser Trp Ala
            180                 185                 190
Leu Ser Ser Gly Glu Gln Trp Cys Glu Arg Ala Ser Pro Pro Ser Ser
        195                 200                 205
Ser Cys Asn Ile Ser Ser Gly Glu Met Gln Lys Gly Leu Trp Glu Gln
        210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
                245                 250                 255
Cys Ala Gly Gly Leu Glu Cys Ala Cys Pro Ala Leu Leu Glu Tyr Ala
            260                 265                 270
Arg Thr Cys Ala Gln Glu Gly Met Val Leu Tyr Gly Trp Thr Asp His
        275                 280                 285
Ser Ala Cys Ser Pro Val Cys Pro Ala Gly Met Glu Tyr Arg Gln Cys
        290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
            340                 345                 350
Ser Gly Lys Arg Tyr Pro Pro Gly Thr Ser Leu Ser Arg Asp Cys Asn
        355                 360                 365
Thr Cys Ile Cys Arg Asn Ser Gln Trp Ile Cys Ser Asn Glu Glu Cys
        370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
            420                 425                 430
Ala Asp Asp Arg Asp Ala Val Cys Thr Arg Ser Val Thr Val Arg Leu
        435                 440                 445
Pro Gly Leu His Asn Ser Leu Val Lys Leu Lys His Gly Ala Gly Val
        450                 455                 460
Ala Met Asp Gly Gln Asp Ile Gln Leu Pro Leu Leu Lys Gly Asp Leu
465                 470                 475                 480
Arg Ile Gln His Thr Val Thr Ala Ser Val Arg Leu Ser Tyr Gly Glu
                485                 490                 495
Asp Leu Gln Met Asp Trp Asp Gly Arg Gly Arg Leu Leu Val Lys Leu
```

-continued

```
            500                 505                 510
Ser Pro Val Tyr Ala Gly Lys Thr Cys Gly Leu Cys Gly Asn Tyr Asn
            515                 520                 525
Gly Asn Gln Gly Asp Asp Phe Leu Thr Pro Ser Gly Leu Ala Glu Pro
        530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
                565                 570                 575
Thr Arg Phe Ser Glu Glu Ala Cys Ala Val Leu Thr Ser Pro Thr Phe
            580                 585                 590
Glu Ala Cys His Arg Ala Val Ser Pro Leu Pro Tyr Leu Arg Asn Cys
        595                 600                 605
Arg Tyr Asp Val Cys Ser Cys Ser Asp Gly Arg Glu Cys Leu Cys Gly
    610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
                645                 650                 655
Val Tyr Leu Gln Cys Gly Thr Pro Cys Asn Leu Thr Cys Arg Ser Leu
            660                 665                 670
Ser Tyr Pro Asp Glu Glu Cys Asn Glu Ala Cys Leu Glu Gly Cys Phe
        675                 680                 685
Cys Pro Pro Gly Leu Tyr Met Asp Glu Arg Gly Asp Cys Val Pro Lys
    690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Met Ser Gly Val Pro Gly Ser Leu Leu Pro Asp Ala Val
            740                 745                 750
Leu Ser Ser Pro Leu Ser His Arg Ser Lys Arg Ser Leu Ser Cys Arg
        755                 760                 765
Pro Pro Met Val Lys Leu Val Cys Pro Ala Asp Asn Leu Arg Ala Glu
    770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
                805                 810                 815
His Glu Asn Arg Cys Val Ala Leu Glu Arg Cys Pro Cys Phe His Gln
            820                 825                 830
Gly Lys Glu Tyr Ala Pro Gly Glu Thr Val Lys Ile Gly Cys Asn Thr
        835                 840                 845
Cys Val Cys Arg Asp Arg Lys Trp Asn Cys Thr Asp His Val Cys Asp
    850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Phe Arg Ile Leu Val Gly Asn Lys
            900                 905                 910
Gly Cys Ser His Pro Ser Val Lys Cys Lys Lys Arg Val Thr Ile Leu
        915                 920                 925
```

```
Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp Gly Ile Gln Asn Asn Asp Leu Thr
            995                 1000                1005

Ser Ser Asn Leu Gln Val Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335
```

```
Glu Leu Arg Arg Ile Ala Ser Gln Val Lys Tyr Ala Gly Ser Gln
    1340            1345                1350

Val Ala Ser Thr Ser Glu Val Leu Lys Tyr Thr Leu Phe Gln Ile
    1355            1360                1365

Phe Ser Lys Ile Asp Arg Pro Glu Ala Ser Arg Ile Ala Leu Leu
    1370            1375                1380

Leu Met Ala Ser Gln Glu Pro Gln Arg Met Ser Arg Asn Phe Val
    1385            1390                1395

Arg Tyr Val Gln Gly Leu Lys Lys Lys Val Ile Val Ile Pro
    1400            1405                1410

Val Gly Ile Gly Pro His Ala Asn Leu Lys Gln Ile Arg Leu Ile
    1415            1420                1425

Glu Lys Gln Ala Pro Glu Asn Lys Ala Phe Val Leu Ser Ser Val
    1430            1435                1440

Asp Glu Leu Glu Gln Gln Arg Asp Glu Ile Val Ser Tyr Leu Cys
    1445            1450                1455

Asp Leu Ala Pro Glu Ala Pro Pro Pro Thr Leu Pro Pro His Met
    1460            1465                1470

Ala Gln Val Thr Val Gly Pro Gly Leu Leu Gly Val Ser Thr Leu
    1475            1480                1485

Gly Pro Lys Arg Asn Ser Met Val Leu Asp Val Ala Phe Val Leu
    1490            1495                1500

Glu Gly Ser Asp Lys Ile Gly Glu Ala Asp Phe Asn Arg Ser Lys
    1505            1510                1515

Glu Phe Met Glu Glu Val Ile Gln Arg Met Asp Val Gly Gln Asp
    1520            1525                1530

Ser Ile His Val Thr Val Leu Gln Tyr Ser Tyr Met Val Thr Val
    1535            1540                1545

Glu Tyr Pro Phe Ser Glu Ala Gln Ser Lys Gly Asp Ile Leu Gln
    1550            1555                1560

Arg Val Arg Glu Ile Arg Tyr Gln Gly Gly Asn Arg Thr Asn Thr
    1565            1570                1575

Gly Leu Ala Leu Arg Tyr Leu Ser Asp His Ser Phe Leu Val Ser
    1580            1585                1590

Gln Gly Asp Arg Glu Gln Ala Pro Asn Leu Val Tyr Met Val Thr
    1595            1600                1605

Gly Asn Pro Ala Ser Asp Glu Ile Lys Arg Leu Pro Gly Asp Ile
    1610            1615                1620

Gln Val Val Pro Ile Gly Val Gly Pro Asn Ala Asn Val Gln Glu
    1625            1630                1635

Leu Glu Arg Ile Gly Trp Pro Asn Ala Pro Ile Leu Ile Gln Asp
    1640            1645                1650

Phe Glu Thr Leu Pro Arg Glu Ala Pro Asp Leu Val Leu Gln Arg
    1655            1660                1665

Cys Cys Ser Gly Glu Gly Leu Gln Ile Pro Thr Leu Ser Pro Ala
    1670            1675                1680

Pro Asp Cys Ser Gln Pro Leu Asp Val Ile Leu Leu Leu Asp Gly
    1685            1690                1695

Ser Ser Ser Phe Pro Ala Ser Tyr Phe Asp Glu Met Lys Ser Phe
    1700            1705                1710

Ala Lys Ala Phe Ile Ser Lys Ala Asn Ile Gly Pro Arg Leu Thr
    1715            1720                1725

Gln Val Ser Val Leu Gln Tyr Gly Ser Ile Thr Thr Ile Asp Val
```

-continued

```
                           1730                    1735                    1740

Pro  Trp  Asn  Val  Val  Pro  Glu  Lys  Ala  His  Leu  Leu  Ser  Leu  Val
          1745                    1750                    1755

Asp  Val  Met  Gln  Arg  Glu  Gly  Gly  Pro  Ser  Gln  Ile  Gly  Asp  Ala
     1760                    1765                    1770

Leu  Gly  Phe  Ala  Val  Arg  Tyr  Leu  Thr  Ser  Glu  Met  His  Gly  Ala
     1775                    1780                    1785

Arg  Pro  Gly  Ala  Ser  Lys  Ala  Val  Val  Ile  Leu  Val  Thr  Asp  Val
     1790                    1795                    1800

Ser  Val  Asp  Ser  Val  Asp  Ala  Ala  Ala  Asp  Ala  Ala  Arg  Ser  Asn
     1805                    1810                    1815

Arg  Val  Thr  Val  Phe  Pro  Ile  Gly  Ile  Gly  Asp  Arg  Tyr  Asp  Ala
     1820                    1825                    1830

Ala  Gln  Leu  Arg  Ile  Leu  Ala  Gly  Pro  Ala  Gly  Asp  Ser  Asn  Val
     1835                    1840                    1845

Val  Lys  Leu  Gln  Arg  Ile  Glu  Asp  Leu  Pro  Thr  Met  Val  Thr  Leu
     1850                    1855                    1860

Gly  Asn  Ser  Phe  Leu  His  Lys  Leu  Cys  Ser  Gly  Phe  Val  Arg  Ile
     1865                    1870                    1875

Cys  Met  Asp  Glu  Asp  Gly  Asn  Glu  Lys  Arg  Pro  Gly  Asp  Val  Trp
     1880                    1885                    1890

Thr  Leu  Pro  Asp  Gln  Cys  His  Thr  Val  Thr  Cys  Gln  Pro  Asp  Gly
     1895                    1900                    1905

Gln  Thr  Leu  Leu  Lys  Ser  His  Arg  Val  Asn  Cys  Asp  Arg  Gly  Leu
     1910                    1915                    1920

Arg  Pro  Ser  Cys  Pro  Asn  Ser  Gln  Ser  Pro  Val  Lys  Val  Glu  Glu
     1925                    1930                    1935

Thr  Cys  Gly  Cys  Arg  Trp  Thr  Cys  Pro  Cys  Val  Cys  Thr  Gly  Ser
     1940                    1945                    1950

Ser  Thr  Arg  His  Ile  Val  Thr  Phe  Asp  Gly  Gln  Asn  Phe  Lys  Leu
     1955                    1960                    1965

Thr  Gly  Ser  Cys  Ser  Tyr  Val  Leu  Phe  Gln  Asn  Lys  Glu  Gln  Asp
     1970                    1975                    1980

Leu  Glu  Val  Ile  Leu  His  Asn  Gly  Ala  Cys  Ser  Pro  Gly  Ala  Arg
     1985                    1990                    1995

Gln  Gly  Cys  Met  Lys  Ser  Ile  Glu  Val  Lys  His  Ser  Ala  Leu  Ser
     2000                    2005                    2010

Val  Glu  Leu  His  Ser  Asp  Met  Glu  Val  Thr  Val  Asn  Gly  Arg  Leu
     2015                    2020                    2025

Val  Ser  Val  Pro  Tyr  Val  Gly  Gly  Asn  Met  Glu  Val  Asn  Val  Tyr
     2030                    2035                    2040

Gly  Ala  Ile  Met  His  Glu  Val  Arg  Phe  Asn  His  Leu  Gly  His  Ile
     2045                    2050                    2055

Phe  Thr  Phe  Thr  Pro  Gln  Asn  Asn  Glu  Phe  Gln  Leu  Gln  Leu  Ser
     2060                    2065                    2070

Pro  Lys  Thr  Phe  Ala  Ser  Lys  Thr  Tyr  Gly  Leu  Cys  Gly  Ile  Cys
     2075                    2080                    2085

Asp  Glu  Asn  Gly  Ala  Asn  Asp  Phe  Met  Leu  Arg  Asp  Gly  Thr  Val
     2090                    2095                    2100

Thr  Thr  Asp  Trp  Lys  Thr  Leu  Val  Gln  Glu  Trp  Thr  Val  Gln  Arg
     2105                    2110                    2115

Pro  Gly  Gln  Thr  Cys  Gln  Pro  Ile  Leu  Glu  Glu  Gln  Cys  Leu  Val
     2120                    2125                    2130
```

```
Pro Asp Ser Ser His Cys Gln Val Leu Leu Pro Leu Phe Ala
2135            2140              2145

Glu Cys His Lys Val Leu Ala Pro Ala Thr Phe Tyr Ala Ile Cys
2150            2155              2160

Gln Gln Asp Ser Cys His Gln Glu Gln Val Cys Glu Val Ile Ala
2165            2170              2175

Ser Tyr Ala His Leu Cys Arg Thr Asn Gly Val Cys Val Asp Trp
2180            2185              2190

Arg Thr Pro Asp Phe Cys Ala Met Ser Cys Pro Pro Ser Leu Val
2195            2200              2205

Tyr Asn His Cys Glu His Gly Cys Pro Arg His Cys Asp Gly Asn
2210            2215              2220

Val Ser Ser Cys Gly Asp His Pro Ser Glu Gly Cys Phe Cys Pro
2225            2230              2235

Pro Asp Lys Val Met Leu Glu Gly Ser Cys Val Pro Glu Glu Ala
2240            2245              2250

Cys Thr Gln Cys Ile Gly Glu Asp Gly Val Gln His Gln Phe Leu
2255            2260              2265

Glu Ala Trp Val Pro Asp His Gln Pro Cys Gln Ile Cys Thr Cys
2270            2275              2280

Leu Ser Gly Arg Lys Val Asn Cys Thr Thr Gln Pro Cys Pro Thr
2285            2290              2295

Ala Lys Ala Pro Thr Cys Gly Leu Cys Glu Val Ala Arg Leu Arg
2300            2305              2310

Gln Asn Ala Asp Gln Cys Cys Pro Glu Tyr Glu Cys Val Cys Asp
2315            2320              2325

Pro Val Ser Cys Asp Leu Pro Pro Val Pro His Cys Glu Arg Gly
2330            2335              2340

Leu Gln Pro Thr Leu Thr Asn Pro Gly Glu Cys Arg Pro Asn Phe
2345            2350              2355

Thr Cys Ala Cys Arg Lys Glu Glu Cys Lys Arg Val Ser Pro Pro
2360            2365              2370

Ser Cys Pro Pro His Arg Leu Pro Thr Leu Arg Lys Thr Gln Cys
2375            2380              2385

Cys Asp Glu Tyr Glu Cys Ala Cys Asn Cys Val Asn Ser Thr Val
2390            2395              2400

Ser Cys Pro Leu Gly Tyr Leu Ala Ser Thr Ala Thr Asn Asp Cys
2405            2410              2415

Gly Cys Thr Thr Thr Thr Cys Leu Pro Asp Lys Val Cys Val His
2420            2425              2430

Arg Ser Thr Ile Tyr Pro Val Gly Gln Phe Trp Glu Glu Gly Cys
2435            2440              2445

Asp Val Cys Thr Cys Thr Asp Met Glu Asp Ala Val Met Gly Leu
2450            2455              2460

Arg Val Ala Gln Cys Ser Gln Lys Pro Cys Glu Asp Ser Cys Arg
2465            2470              2475

Ser Gly Phe Thr Tyr Val Leu His Glu Gly Glu Cys Cys Gly Arg
2480            2485              2490

Cys Leu Pro Ser Ala Cys Glu Val Val Thr Gly Ser Pro Arg Gly
2495            2500              2505

Asp Ser Gln Ser Ser Trp Lys Ser Val Gly Ser Gln Trp Ala Ser
2510            2515              2520

Pro Glu Asn Pro Cys Leu Ile Asn Glu Cys Val Arg Val Lys Glu
2525            2530              2535
```

```
Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 4
<211> LENGTH: 45
<212> TYPE: DNA
<213> ORGANISM: Homo sapiens

<400> SEQUENCE: 4
ggtaatgagg gtcgcgagaa cctttatttc cagggccagg cgccc            45

<210> SEQ ID NO 5
<211> LENGTH: 38
<212> TYPE: DNA
<213> ORGANISM: Homo sapiens

<400> SEQUENCE: 5
agaggagagt tagagcctca cctctgcagc accaggtc                    38

<210> SEQ ID NO 6
<211> LENGTH: 9
```

```
<212> TYPE: PRT
<213> ORGANISM: Homo sapiens

<400> SEQUENCE: 6

Glu Ala Pro Asp Leu Val Leu Gln Arg
1               5
```